(12) United States Patent
Kotanko et al.

(10) Patent No.: US 10,525,186 B2
(45) Date of Patent: Jan. 7, 2020

(54) METHODS OF REGIONAL CITRATE ANTICOAGULATION DIALYSIS

(71) Applicant: Fresenius Medical Care Holdings, Inc., Waltham, MA (US)

(72) Inventors: Peter Kotanko, New York, NY (US); Stephan Thijssen, New York, NY (US); Nathan W. Levin, New York, NY (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 955 days.

(21) Appl. No.: 14/463,000

(22) Filed: Aug. 19, 2014

(65) Prior Publication Data

US 2014/0353251 A1 Dec. 4, 2014

Related U.S. Application Data

(62) Division of application No. 12/817,390, filed on Jun. 17, 2010, now Pat. No. 8,845,571.

(Continued)

(51) Int. Cl.
*A61M 1/34* (2006.01)
*A61M 1/16* (2006.01)
*A61M 1/36* (2006.01)

(52) U.S. Cl.
CPC ............ *A61M 1/3458* (2014.02); *A61M 1/16* (2013.01); *A61M 1/1613* (2014.02);
(Continued)

(58) Field of Classification Search
CPC .... A61M 1/16; A61M 1/1613; A61M 1/1656; A61M 1/3458; A61M 1/3672; A61M 1/1654; A61M 1/3675
See application file for complete search history.

(56) References Cited

U.S. PATENT DOCUMENTS 3,941,565 A 3/1976 Schwartz
4,000,072 A 12/1976 Sato et al.
(Continued)

FOREIGN PATENT DOCUMENTS

CN 1328467 A 12/2001
CN 101184517 A 5/2008
(Continued)

OTHER PUBLICATIONS

Daugirdas, J.T., et al., *Handbook of Dialysis*, pp. 204-251 (2007).
(Continued)

*Primary Examiner* — Ariana Zimbouski
(74) *Attorney, Agent, or Firm* — Hamilton, Brook, Smith & Reynolds, P.C.

(57) ABSTRACT

A method of performing regional citrate anticoagulant dialysis of a patient's blood includes flowing blood from and back to the patient through an extracorporeal circuit including a dialyzer having semi-permeable dialysis membranes and a dialysate chamber surrounding the membranes. The method further includes flowing a dialysate containing calcium and citrate through the dialysate chamber of the dialyzer and introducing citrate into the patient's blood upstream of the dialyzer, whereby the patient's blood is dialyzed. The method can further include predicting the concentration of systemic ionized calcium in the blood of the patient at any point in the dialysis treatment or post-dialysis, such as by a mathematical model. The method can further include statistically correcting the preliminary predicted post-dialysis concentration of systemic ionized calcium in the patient's blood to provide a final predicted post-dialysis systemic ionized calcium concentration. The method can further include statistically correcting the preliminary predicted systemic ionized calcium concentration for any time point (Continued)

during the dialysis treatment to provide a final predicted systemic ionized calcium concentration for that time point.

24 Claims, 12 Drawing Sheets

Related U.S. Application Data

(60) Provisional application No. 61/335,546, filed on Jan. 8, 2010, provisional application No. 61/268,871, filed on Jun. 17, 2009.

(52) U.S. Cl.
CPC ........ *A61M 1/1654* (2013.01); *A61M 1/3672* (2013.01); *A61M 1/3675* (2013.01); *A61M 1/1656* (2013.01); *A61M 2230/20* (2013.01)

(56) References Cited

U.S. PATENT DOCUMENTS

| | | | |
|---|---|---|---|
| 5,437,864 A | 8/1995 | Edgington et al. | |
| 5,730,713 A | 3/1998 | Okarma et al. | |
| 6,200,287 B1 | 3/2001 | Keller et al. | |
| 6,368,785 B1* | 4/2002 | Ranby | A61K 35/14 435/2 |
| 6,610,206 B1 | 8/2003 | Callan et al. | |
| 7,351,218 B2 | 4/2008 | Bene | |
| 7,862,530 B2 | 1/2011 | Callan et al. | |
| 8,414,768 B2 | 4/2013 | Shah et al. | |
| 8,845,571 B2 | 9/2014 | Kotanko et al. | |
| 8,911,390 B2* | 12/2014 | Sternby | A61K 31/191 210/645 |
| 2004/0048837 A1 | 3/2004 | Lazarus | |
| 2004/0060865 A1 | 4/2004 | Callan et al. | |
| 2004/0133145 A1* | 7/2004 | Bene | A61M 1/342 604/5.01 |
| 2004/0230152 A1 | 11/2004 | Bainbridge et al. | |
| 2005/0119598 A1* | 6/2005 | Callan | A61K 31/19 604/5.01 |
| 2005/0236330 A1 | 10/2005 | Nier et al. | |
| 2007/0062861 A1 | 3/2007 | Lannoy | |
| 2007/0066928 A1* | 3/2007 | Lannoy | A61M 1/16 604/6.07 |
| 2007/0270341 A1 | 11/2007 | Morley et al. | |
| 2008/0015487 A1 | 1/2008 | Szamosfalvi et al. | |
| 2008/0280955 A1 | 11/2008 | McCamish | |
| 2011/0237996 A1 | 9/2011 | Kotanko et al. | |

FOREIGN PATENT DOCUMENTS

| | | |
|---|---|---|
| DE | 19654746 A1 | 7/1998 |
| EP | 1 430 920 A1 | 6/2004 |
| WO | WO 2007/101064 A2 | 9/2007 |
| WO | WO 2009/026603 A1 | 3/2009 |
| WO | WO 2010/029401 A2 | 3/2010 |
| WO | WO 2010/112538 A1 | 10/2010 |

OTHER PUBLICATIONS

Bohler, J., et al., "Reduction of Granulocyte Activation During Hemodialysis with Regional Citrate Anticoagulation: Dissociation of Complement Activation and Neutropenia from Neutrophil Degranulation," *J. Am. Soc. Nephrol.*, 7:234-241 (1996).

Gabutti, L., et al., "The Favorable Effect of Regional Citrate Anticoagulation on Interleukin-1 Beta Release is Dissociated from Both Coagulation and Complement Activation," *J. Nephrol.*, 17:819-825 (2004).

Glitters, M., et al., "Citrate Anticoagulation Abolishes Degranulation of Polymorphonuclear Cells and Platelets and Reduces Oxidative Stress During Haemodialysis," *Nephrol. Dial. Transplant*, 21:153-159 (2006).

Hofbauer, R., et al., "Effect of Anticoagulation on Blood Membrane Interactions During Hemodialysis," *Kidney Int.*, 56:1578-1583 (1999).

Dittrich, et al., *J. Am. Soc. Nephrol.*, 19, pp. 461A, Abstract F-PO1576 (2008).

Kozik-Jaromin, J., "Citrate Kinetics During Regional Citrate Anticoagulation in Extracorporeal Organ Replacement Therapy," *Internal Medicine, IV, Nephrology* (2005).

International Search Report and Written Opinion, PCT/US2010/038985, dated Oct. 5, 2010.

International Preliminary Report on Patentability issued in International Application No. PCT/US2010/038985; dated Dec. 20, 2011.

Evenepoel, et al., Regional Citrate Anticoagulation for Hemodialysis Using a Conventional Calcium-Containing Dialysate, *Am. J. Kidney Dis.*, 39: 315-323 (2002).

Notice of Allowance, U.S. Appl. No. 12/817,390, dated Jun. 12, 2014.

Interview Summary, U.S. Appl. No. 12/817,390, dated Feb. 11, 2014.

Non-Final Office Action, U.S. Appl. No. 12/817,390, dated Oct. 24, 2013.

Final Office Action, U.S. Appl. No. 12/817,390, dated Jul. 5, 2013.

Interview Summary, U.S. Appl. No. 12/817,390, dated May 22, 2013.

Final Office Action, U.S. Appl. No. 12/817,390, dated Feb. 28, 2013.

Non-Final Office Action, U.S. Appl. No. 12/817,390, dated Jul. 20, 2012.

* cited by examiner

| | Top-level overview of basic RCA model components and corresponding key calculations | |
|---|---|---|
| sys | Calculate citrate generation and metabolism to determine resulting citrate and calcium equilibria | Ci metabolization: $C\_Ci(t) = C0 * exp(-k*t)$; Ci generation: $C\_Ci = Rate\_Ci\_generation * interval\_length$ |
| 1 | Calculate citrate and calcium concentration changes caused by recirculation | Known techniques in the art. |
| 2 | Calculate pre-dialyzer Ci concentration required to achieve target pre-dialyzer ionized calcium concentration. | C_bindingsites according to C_protein and 12 binding sites per molecule of albumin; $C\_CiT = (-C\_Cafree \wedge 3 - C\_Cafree \wedge 2 * K\_CaCi - C\_Cafree \wedge 2 * K\_CaP - C\_Cafree \wedge 2 * C\_bindingsites + C\_Cafree \wedge 2 + C\_CaT - C\_Cafree * K\_CaCi * K\_CaP - C\_Cafree * K\_CaCi * C\_bindingsites + C\_Cafree * K\_CaCi * C\_CaT + C\_Cafree * K\_CaP * C\_CaT + K\_CaCi * K\_CaP * C\_CaT + C\_Cafree * K\_CaP * C\_CaT + K\_CaCi * K\_CaP * C\_CaT) / (C\_Cafree \wedge 2 + C\_Cafree * K\_CaP); C\_CaCi = ((C\_Cafree * C\_CiT)) / (K\_CaCi + C\_Cafree))$ |
| 3 | Calculate diffusive and convective dialyzer fluxes | Mass transfer area coefficients from literature or own data. Dialysance calculations and convective clearances according to known techniques in the art. |
| 3 | Calculate post-dialyzer citrate and calcium concentrations | According to trans-membrane mass balances and solute distribution volume changes, then as per calculations in step 3 and: $C\_Cifree = C\_CiT - C\_CaCi$ |
| 4 | Calculate citrate and calcium concentrations post Ca infusion (optional) | $C\_CaT$ = self-evident; $C\_CiT$ and $C\_bindingsites$ = self-evident (as per volume expansion); $C\_Cafree$ and $C\_CaCi$ as per calculations in step 3; $C\_Cifree = C\_CiT - C\_CaCi$ |
| 5 | Calculate dialysate composition | $C\_Cifree = -0.5 * (C\_CaT - C\_CiT + K\_CaCi) + Sqrt((0.5 * (C\_CaT - C\_CiT + K\_CaCi))\wedge 2 + (K\_CaCi * C\_CiT)); C\_Cafree = C\_CaT$ OR $(K\_CaCi * (C\_CiT - C\_Cifree)) / C\_Cifree$ (if Ci-containing dialysate); $C\_CaCi = (C\_Cafree * C\_Cifree) / K\_CaCi$ |

FIG. 3A

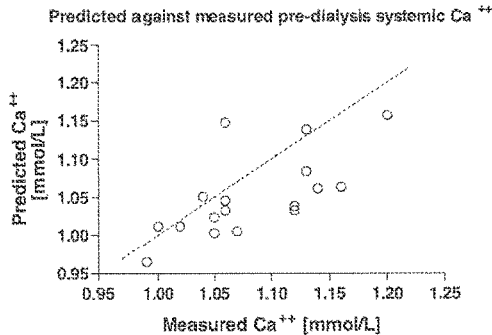
FIG. 4A
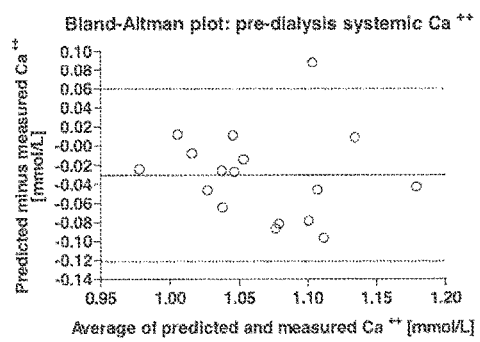
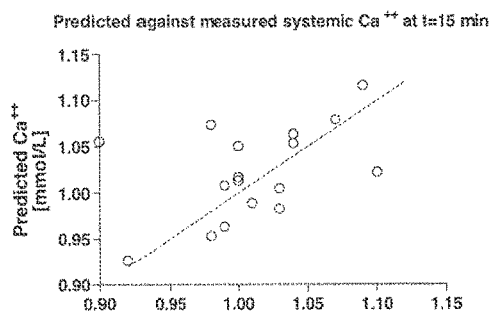
FIG. 4B
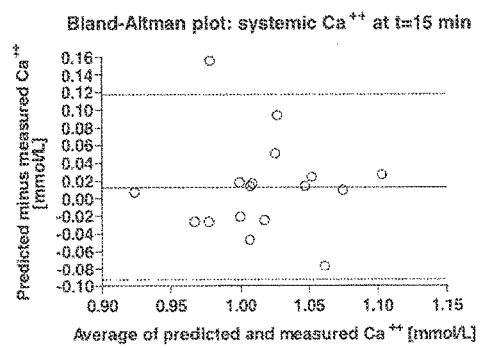
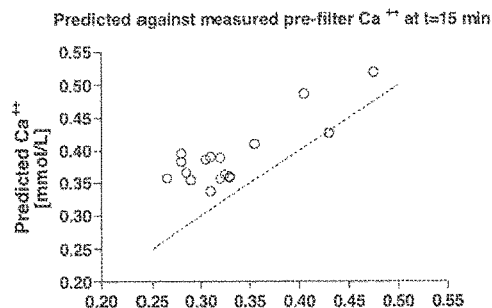
FIG. 4C
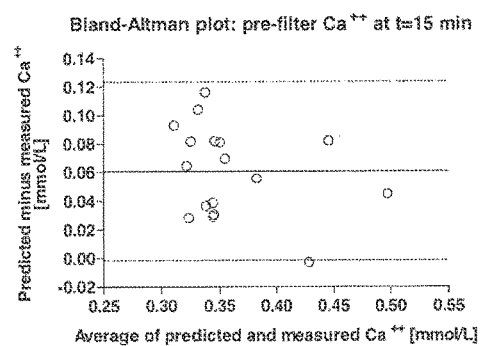
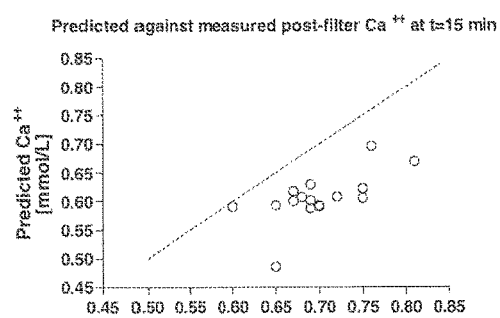
FIG. 4D
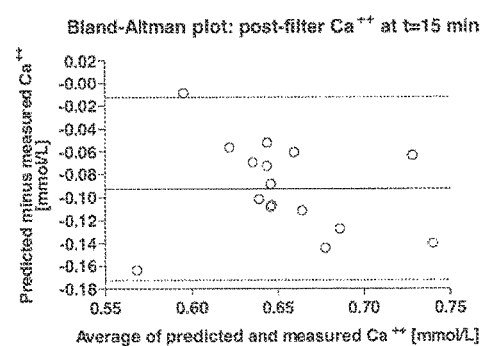

METHODS OF REGIONAL CITRATE ANTICOAGULATION DIALYSIS

RELATED APPLICATIONS

This application is a Divisional of U.S. application Ser. No. 12/817,390, filed on Jun. 17, 2010, which claims the benefit of U.S. Provisional Application No. 61/268,871, filed on Jun. 17, 2009 and U.S. Provisional Application No. 61/335,546, filed on Jan. 8, 2010.

The entire teachings of the above applications are incorporated herein by reference.

BACKGROUND OF THE INVENTION

Renal dysfunction or failure and, in particular, end-stage renal disease, causes the body to lose the ability to remove water and minerals and excrete harmful metabolites, maintain acid-base balance and control electrolyte and mineral concentrations within physiological ranges. Toxic uremic waste metabolites including urea, creatinine, and uric acid accumulate in the body's tissues which can result in a person's death if the filtration function of the kidney is not replaced.

Dialysis is commonly used to replace kidney function by removing these waste toxins and excess water. In one type of dialysis treatment—hemodialysis (HD)—toxins are filtered from a patient's blood externally in a hemodialysis machine. Blood passes from the patient through a dialyzer separated by a semi-permeable membrane from a large volume of externally-supplied dialysate. Typically, the blood passes through the inside of semi-permeable hollow fibers, and the dialysate flows on the outside of the semi-permeable hollow fibers in a countercurrent direction. The waste and toxins dialyze out of the blood through the semi-permeable membrane into the dialysate, which is then discarded.

The patient's blood is exposed to intravenous cannulas, tubing, drip chambers, headers, potting compound, and dialysis membranes during the dialysis procedure. These surfaces exhibit a variable degree of thrombogenicity and may initiate clotting of blood, especially in conjunction with exposure of blood to air in drip chambers. The resulting thrombus formation may be significant enough to cause occlusion and malfunction of the extracorporeal circuit. See J. T. Daugirdas, P. G. Blake, and T. S. Ing, *Handbook of Dialysis*, (2007).

One method of preventing blood clotting is to administer heparin to the patient, shortly before or during the dialysis treatment. Heparin, however, has potential undesirable side effects, such as, for example, pruritus, allergy, osteoporosis, hyperlipidemia, thrombocytopenia, and excessive bleeding. Heparin is therefore not recommended for patients at risk of bleeding due to gastrointestinal lesions (gastritis, peptic ulcer, angiodysplasia), recent surgery, or pericarditis.

Another method of preventing blood clotting is regional citrate anticoagulation (RCA), which can be used alone or combined with and potentially reduce heparin administration. RCA has been shown to reduce complement activation, degranulation of granulocytes and platelets and the release of IL-1b, thus improving biocompatibility of the extracorporeal circuit. Bohler J., Schollmeyer P., Dressel B., Dobos G., Horl W. H.: *Reduction of granulocyte activation during hemodialysis with regional citrate anticoagulation: dissociation of complement activation and neutropenia from neutrophil degranulation*. J Am Soc Nephrol 7:234-241. 1996; Gabutti L., Ferrari N., Mombelli G., Keller F., Marone C.: *The favorable effect of regional citrate anticoagulation on interleukin-1 beta release is dissociated from both coagulation and complement activation*. J Nephrol 17:819-825. 2004; Gritters M., Grooteman M. P., Schoorl M., Schoorl M., Bartels P. C., Scheffer P. G., Teerlink T., Schalkwijk C. G., Spreeuwenberg M., Nube M. J.: *Citrate anticoagulation abolishes degranulation of polymorphonuclear cells and platelets and reduces oxidative stress during haemodialysis*. Nephrol Dial Transplant 21:153-159. 2006. The actual anticoagulative effect of RCA in the dialyzer has also been demonstrated to be superior to both unfractionated and low-molecular-weight heparin. Hofbauer R., Moser D., Frass M., Oberbauer R., Kaye A. D., Wagner O., Kapiotis S., Druml W.: *Effect of anticoagulation on blood membrane interactions during hemodialysis*. Kidney Int 56:1578-1583. 1999. More recently, the sharp rise of heparin costs has further spurred interest in RCA as an alternative mode of anticoagulation.

The application of regional citrate anticoagulation (RCA) in hemodialysis classically involves citrate infusion before the hemodialyzer, calcium infusion after the dialyzer, and use of a calcium-free dialysate. The extremely low ionized calcium (iCa) levels generated by infusion of citrate into the arterial line prevent clotting in the extracorporeal circuit but have to be raised again in the venous line before the blood re-enters the patient's systemic circulation. Citrate infusion and calcium infusion have to be balanced carefully in order to avoid systemic hypo- or hypercalcemia in the patient. See U.S. application Ser. No. 12/580,803, filed on Oct. 16, 2009. This requires close monitoring of systemic iCa levels, which is classically accomplished by repetitive blood draws and iCa measurements throughout the dialysis treatment. This is a labor- and material-intensive process.

An attempt to provide heparin-free anticoagulation without the need for citrate infusion and calcium infusion by employing a commercially available dialysate containing both calcium and citrate (Citrasate® citrate dialysate) resulted in clotting of the hemodialyzer in 2 out of 10 cases in one study. Dittrich et al. J Am Soc Nephrol 19 (2008), page 461A, abstract F-PO1576. This demonstrates that Citrasate® citrate dialysate alone does not provide sufficient anticoagulation, which can be ascribed to the iCa concentration along the hollow fibers not being below the level required for adequate anticoagulation.

Therefore, there is a need for a method of preventing blood clotting during a dialysis treatment of a patient that reduces or eliminates the problems described above.

SUMMARY OF THE INVENTION

The invention is generally directed to the combined use of citrate infusion and a dialysate containing both citrate and calcium in dialysis of a patient's blood. This combination enables adequate anticoagulation in the extracorporeal dialysis circuit while the calcium in the dialysate reduces or eliminates the requirement for post-dialyzer calcium infusion.

In one embodiment, a method of performing regional citrate anticoagulant dialysis of a patient's blood includes flowing blood from and back to the patient through an extracorporeal circuit including a dialyzer having semi-permeable dialysis membranes and a dialysate chamber surrounding the membranes. The method further includes flowing a dialysate containing calcium and citrate through the dialysate chamber of the dialyzer and introducing citrate into the patient's blood upstream of the dialyzer in a sufficient amount to reduce clotting of the patient's blood in the extracorporeal dialysis circuit, whereby the patient's blood is dialyzed. In certain embodiments, the amount of calcium contained in the dialysate is sufficient to significantly reduce or eliminate the need for calcium to be added to the patient's blood downstream of the dialyzer. In some embodiments, the citrate can be sodium citrate. In other embodiments, the citrate can be sodium isocitrate. In certain embodiments, the step of introducing the citrate can include time periods when the amount of citrate is modulated downwardly, alternating with time periods when the amount of citrate is modulated upwardly. In some embodiments, the step of introducing the citrate can be computer controlled, including using a processor to computationally determine one or more amounts of citrate during dialysis treatment of a patient, the processor coupled between the patient and the dialyzer. In certain embodiments, the method can further include the step of flushing the dialysis membranes during the time periods when the amount is modulated downwardly. The dialysis membranes can be flushed with a liquid selected from the group consisting of bicarbonate containing dialysate, lactate containing dialysate, acetate containing dialysate, calcium containing dialysate, calcium and citrate anticoagulant containing dialysate, dextrose solutions, and saline. In some embodiments, the step of introducing the citrate can be followed by the step of introducing heparin into the extracorporeal dialysis circuit.

In another embodiment, the method can further include predicting the concentration of systemic ionized calcium in the blood of the patient at any point in the dialysis treatment or post-dialysis. In some embodiments, predicting the concentration of systemic ionized calcium concentration in the blood of the patient is accomplished using a mathematical model. Using a mathematical model can include employing citrate generation and metabolism to determine resulting citrate and calcium equilibria, determining citrate and calcium concentration changes caused by recirculation, determining a required pre-dialyzer citrate concentration and resulting citrate and calcium concentrations, determining a dialysate composition, determining diffusive and convective dialyzer fluxes, and determining post-dialyzer citrate and calcium concentrations. In some embodiments, using a mathematical model can yield a preliminary predicted post-dialysis systemic ionized calcium concentration. The method can further include statistically correcting the preliminary predicted post-dialysis concentration of systemic ionized calcium in the patient's blood to provide a final predicted post-dialysis systemic ionized calcium concentration. Statistically correcting the preliminary predicted post-dialysis concentration of systemic ionized calcium in the patient's blood can include classifying the patient's parathyroid hormone (PTH) level or alkaline phosphatase (AP) level into at least two categories (e.g., tertiles) of PTH or AP levels based on concentration, and estimating a difference between the preliminary predicted and the actual concentration of post-dialysis systemic ionized calcium in the patient's blood based on the category of the PTH or AP level of the patient, dialysis treatment time, and the preliminary predicted post-dialysis concentration of systemic ionized calcium, thereby obtaining a correction to the preliminary predicted post-dialysis concentration of systemic ionized calcium in the patient's blood. The difference between the preliminary predicted and actual concentration of post-dialysis systemic ionized calcium in the patient's blood can be determined by employing a multivariate linear regression model including the category of the PTH or AP level of the patient, dialysis treatment time, and the preliminary predicted post-dialysis concentration of systemic ionized calcium in the patient's blood. In some embodiments, the introduced citrate and the citrate in the dialysate can be individually selected from sodium citrate and sodium isocitrate.

In certain embodiments, estimating the difference between the preliminary predicted concentration and the actual concentration of systemic ionized calcium in the patient's blood can be performed for any time point during dialysis and includes estimating a slope of the relationship between a prediction error, obtained from the preliminary predicted systemic ionized calcium concentration minus the actual measured systemic ionized calcium concentration, and the elapsed time of dialysis, and multiplying the slope by the elapsed time of dialysis for the time point of interest. The prediction error slope can be estimated by employing a multivariate linear regression model including the category (e.g., tertiles) of PTH or AP level of the patient and the preliminary predicted post-dialysis concentration of systemic ionized calcium in the patient's blood as predictors.

In yet another embodiment, a method of modeling a concentration of citrate and calcium in dialyzing blood of a patient includes the computer implemented steps of determining a blood flow rate from and back to the patient through an extracorporeal dialysis circuit including a dialyzer having semi-permeable dialysis membranes and a dialysate chamber surrounding the membranes, determining a flow rate through the dialysate chamber of the dialyzer of a dialysate that includes a predetermined amount of calcium and a predetermined amount of citrate, and computing an amount of citrate anticoagulant to be introduced into the blood, upstream of the dialyzer, such that ionized calcium is reduced upstream of the dialyzer to a concentration that is sufficiently small to reduce clotting of the flowing blood. The method can further include computing a serum concentration of ionized calcium in the blood of the patient, and computing a concentration of citrate in the blood of the patient. In some embodiments, computing the amount of citrate anticoagulant to be introduced includes computationally determining for a given patient certain time periods when the amount of citrate is to be modulated downwardly, and alternating time periods when the amount of citrate is to be modulated upwardly. In certain embodiments, the method is employed during dialysis treatment of a patient. The method can further include maintaining or adjusting the patient's intradialytic calcium mass balance to desired levels relative to the patient's interdialytic intakes of calcium during a time in which the patient is undergoing dialysis treatment using a dialyzer that includes a dialysate containing a calcium concentration by determining a desired calcium mass balance for the patient over a complete dialysis cycle, calculating an intradialytic calcium mass balance, and adjusting the amount of the citrate to be introduced into the blood. The method can further include adjusting the amount of ionized calcium in the dialysate, and adjusting the amount of citrate in the dialysate.

This invention has many advantages, including potentially eliminating well-known downsides of heparin anticoagulation (such as heparin drug side effects, and increased bleeding risk), and addressing critical shortcomings of classic RCA. For example, since no separate calcium infusion may be required, there would be no need for a separate infusion pump, which would make RCA less costly and less laborious compared to current state of the art RCA. The frequent monitoring of systemic iCa and subsequent adjustments of the calcium infusion rate are also potentially rendered obsolete, which eliminates the potential for equipment failure and user error, resulting in improved patient safety.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 3A is a top-level overview of basic regional citrate anticoagulation model components of the invention and corresponding key calculations.

FIGS. 4A-D are graphs of predicted systemic iCa (mmol/L) as a function of measured systemic iCa and the corresponding Bland-Altman graphs.

FIG. 5A results are classified by tertiles of alkaline phosphatase (AP); FIG. 5B results are classified by tertiles of PTH concentration. The one treatment in the high AP and high PTH tertiles that does not cluster with the rest of the group was the one treatment using a dialysate with 2.5 mEq/L calcium concentration, as compared to 3.0 mEq/L for all other treatments.

DETAILED DESCRIPTION OF THE INVENTION

Figure 1:
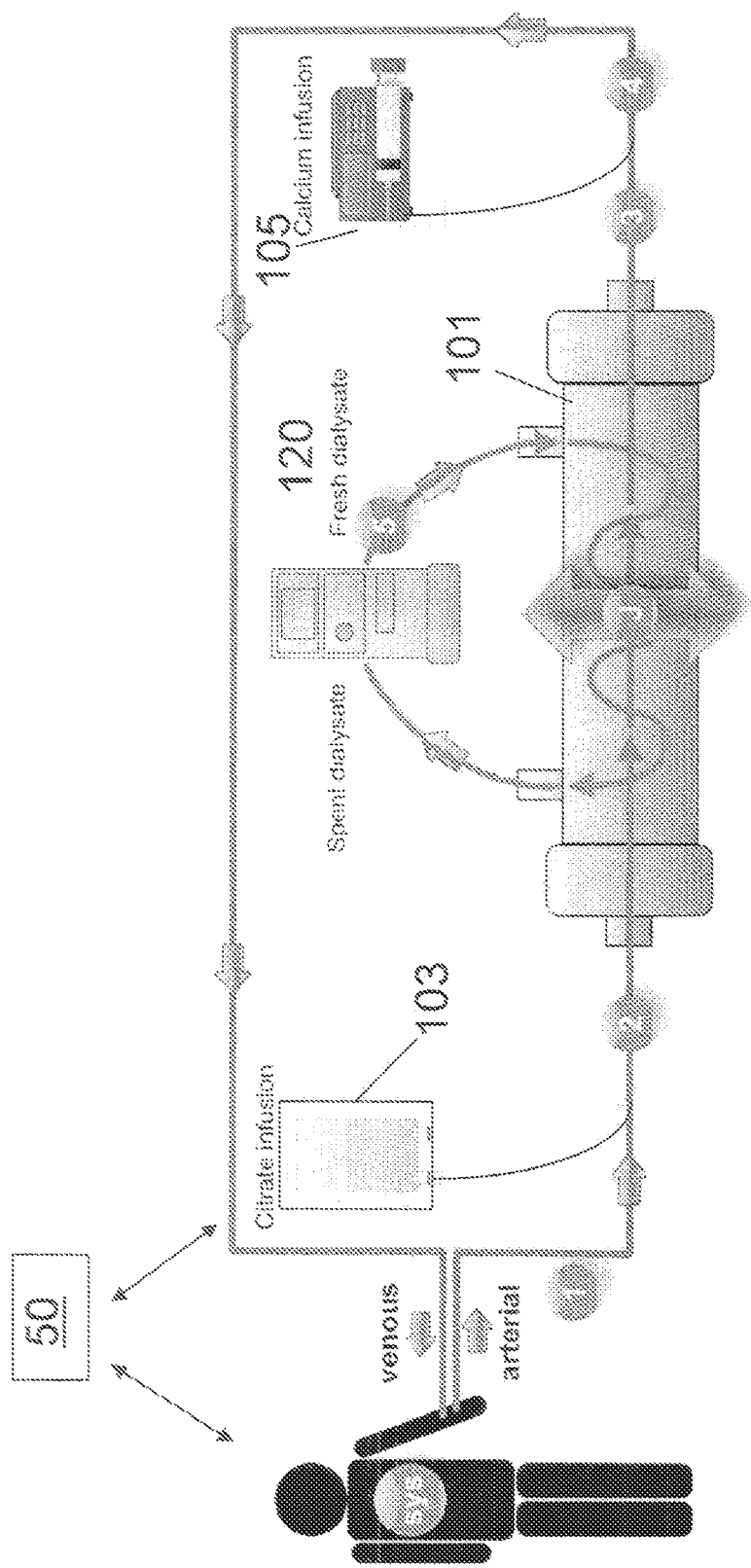
FIG. 1 is a schematic diagram of an extracorporeal dialysis circuit employed in this invention.

Turning to FIG. 1, in one embodiment, a method of performing regional citrate anticoagulant dialysis of a patient's blood includes flowing blood from and back to the patient through an extracorporeal circuit including a dialyzer 101 having semi-permeable dialysis membranes and a dialysate chamber surrounding the membranes. The semi-permeable dialysis membranes can be arranged in various configurations, such as, for example, bundles of hollow fibers made of a polymer, such as, for example, polysulfone. The blood flow rate through the extracorporeal dialysis circuit can be in a range of about 100 ml/min to about 1000 ml/min, preferably in a range of about 400 ml/min to about 500 ml/min.

The method further includes flowing a dialysate 120 containing calcium and citrate through the dialysate chamber of the dialyzer 101, preferably in a counter-current fashion. The amount of calcium contained in the dialysate 120 is sufficient to reduce the need for calcium to be added to the patient's blood downstream of the dialyzer, including eliminating the need for calcium to be added. A commercially available dialysate containing calcium and citrate is Citrasate® citrate dialysate. See U.S. Pat. No. 6,610,206 to Callanan et al. issued Aug. 26, 2003, and U.S. patent application Ser. No. 10/606,150 of Callanan et al. published as U.S. 2004/0060865 on Apr. 1, 2004.

The method further includes introducing citrate (at 103) into the patient's blood upstream of the dialyzer 101 in a sufficient amount to reduce clotting of the patient's blood in the extracorporeal dialysis circuit, whereby the patient's blood is dialyzed. The citrate 103 that is introduced into the patient's blood can be the same citrate that is present in the dialysate, or it can be a different citrate. Examples of citrates are sodium citrate and sodium isocitrate. See U.S. Pat. No. 6,368,785 to Ranby, issued Apr. 9, 2002. The citrate complexes with calcium, reducing the concentration of ionized calcium in the blood of the patient, preventing the blood from clotting. The target ionized calcium concentration pre-dialyzer (after citrate infusion) for traditional regional citrate anticoagulation is in a range of about 0.1 to about 0.4 mmol/L (0.2 to about 0.8 mEq/L). The methods described herein enable a higher concentration of ionized calcium, especially in combination with reduced heparin (e.g., about 50% of standard heparin dose), such as, for example, up to about 0.8 mmol/L (1.6 mEq/L). The dialysate 120 can contain citrate in a range of about 0.5 to about 5 mEq/L, preferably in a range of about 2 to about 4 mEq/L, and calcium in a range of about 1 to about 5 mEq/L, preferably in a range of about 2 to about 4 mEq/L. A commercially available suitable citrate solution has a sodium citrate concentration of about 0.136 M (4%).

Figure 2:
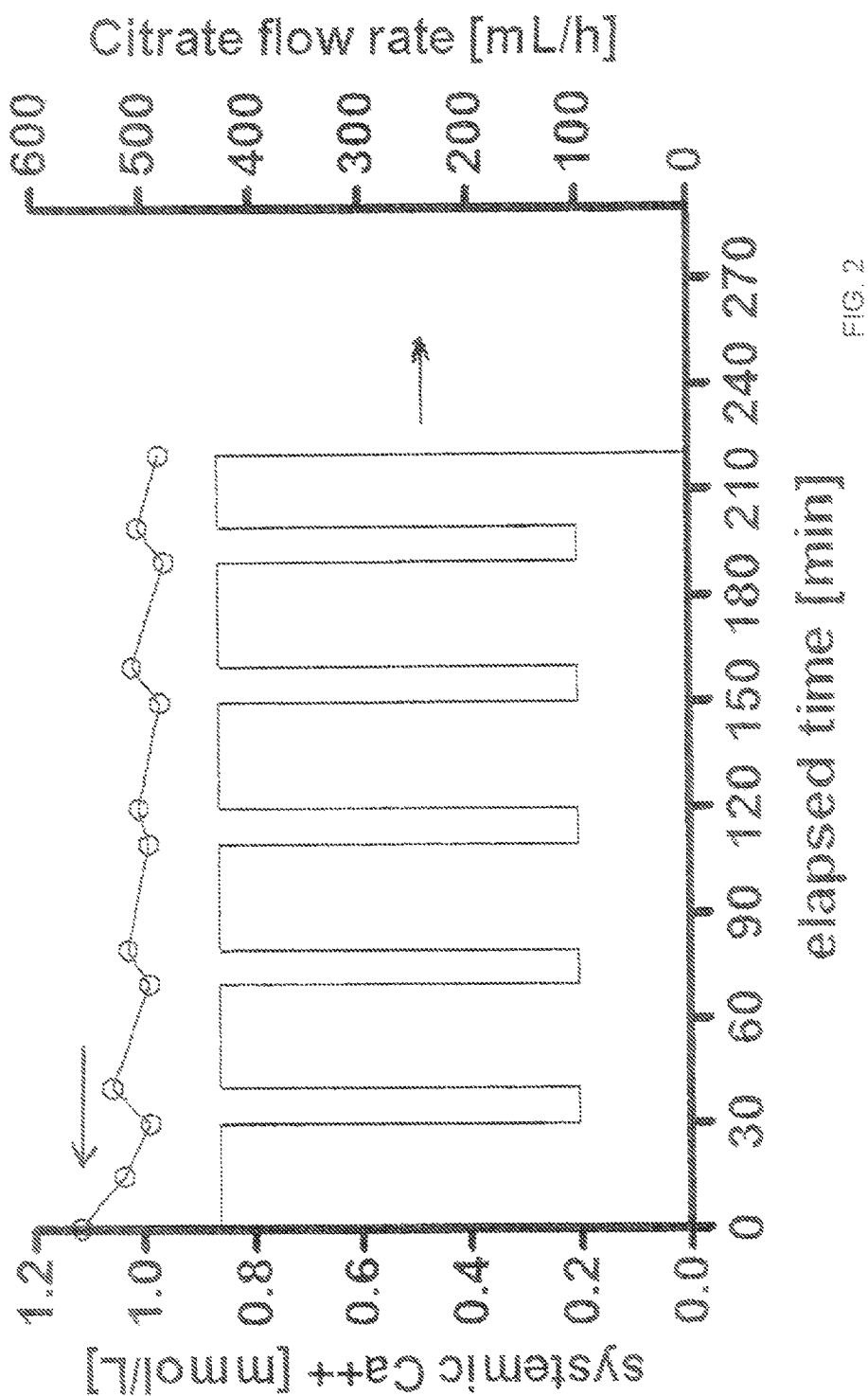
FIG. 2 is a graph of a patient's ionized calcium concentration (left-hand scale) as a function of elapsed time during a dialysis treatment that included the modulations in citrate flow rate shown (right-hand scale).

The methods described herein are computer controlled with computational or mathematical modeling through one or more computer workstations 50 or a computer network, further made clear below. Briefly, computer 50 controls citrate infusion 103 and calcium infusion 105 based on detected (monitored) infusion profiles (described below), calculated citrate and calcium concentrations (pre- and post-dialyzer, after recirculation, etc.), blood flow rate, and dialysate flow rate as input to or otherwise obtained by computer 50. Turning to FIG. 2, in certain embodiments, the step of introducing the citrate includes time periods when the amount of citrate is modulated downwardly, alternating with time periods when the amount of citrate is modulated upwardly. A patient's serum (systemic) ionized calcium level drops during a dialysis treatment using regional citrate anticoagulation, but as shown in FIG. 2, it recovers quickly (e.g., within minutes) after significantly reducing the citrate introduction (infusion), depending on the patient's ionized calcium buffering capacity. This method can be used with patients whose systemic iCa levels tend to decline toward the safety threshold. In such cases, various forms of citrate infusion profiles can be employed, an example of which is shown in FIG. 2, to allow intermittent (partial) recovery of systemic iCa concentrations while still maintaining sufficient anticoagulation over the course of the treatment. Short interruptions of citrate infusion do not immediately lead to clotting of the extracorporeal circuit. Such profiles can take any particular form, including, for example, gradual changes with different slopes, or on-off patterns, or the pattern shown in FIG. 2, where the citrate flow rate is repeatedly modulated from about 425 ml/hr to about 100 ml/hr.

In these embodiments, the method can include the step of flushing the dialysis membranes, for example, during the time periods when the amount is modulated downwardly. Utilization of citrate profiles as described above provides improved systemic iCa stability, but may produce an increased risk of coagulation of the extracorporeal circuit during the low citrate infusion rate periods. Manual, or preferably automated flushes of the blood side of the extracorporeal circuit during those periods can be used to reduce this clotting risk. Such flushes can be used once or repeatedly. The dialysis membranes can be flushed with a liquid selected, for example, from the group consisting of bicarbonate containing dialysate, lactate containing dialysate, acetate containing dialysate, calcium containing dialysate, calcium and citrate containing dialysate, saline, dextrose solutions, and calcium containing solutions. In a preferred embodiment, a diverted stream of inlet dialysate can be used for flushing the blood side of the extracorporeal circuit. Alternatively, the flushing solution can come from a separate source. The flow rate of the flushing solution would be selected so as to not exceed permissible pressures in the extracorporeal circuit. One particular embodiment involves a reduction of the blood flow rate during the flushes in parallel with an increased flow rate of the flushing solution, so that the blood/flushing solution mixture is made up of a greater fraction of flushing solution, while still not exceeding permissible pressures in the extracorporeal circuit. A person skilled in the art of dialysis will recognize that the delivered flushing volume would need to be removed by ultrafiltration. Alternatively, the flushing procedure can involve temporarily bypassing the blood around the dialyzer, for example by using two four-way valves, and flushing the blood side of the dialyzer with a flushing solution without thereby diluting the blood of the patient.

In some embodiments, the step of introducing the citrate can be accompanied by the step of introducing heparin into the extracorporeal circuit. The heparin can be added either as a constant infusion in the arterial line, by using for example a pump, or by injection of an amount of heparin (a bolus) into the arterial line or the venous line of the extracorporeal circuit. The target amount of heparin to be introduced into the extracorporeal circuit can be less than about 1500 units, and preferably less than about 1000 units, which is substantially less than the 3000-5000 units typically used in a dialysis treatment, thereby reducing or eliminating the negative side effects of heparin, including reducing systemic anti-coagulation (i.e., anti-coagulation of the blood in the patient) during and post-dialysis, and yielding significant cost savings.

In another embodiment, the method can further include predicting the concentration of systemic ionized calcium in the blood of the patient. In some embodiments, predicting the concentration of systemic ionized calcium concentration in the blood of the patient is accomplished using a mathematical model, for example, the one illustrated in FIG. 3A, where the steps (sys, 1, 2, J, 3-5) are labeled to correspond to the labels shown in FIG. 1. Using a mathematical model can include employing citrate generation and metabolism to determine resulting citrate and calcium equilibria, determining citrate and calcium concentration changes caused by recirculation, determining a required pre-dialyzer citrate concentration and resulting citrate and calcium concentrations, determining a dialysate composition, determining diffusive and convective dialyzer fluxes, and determining post-dialyzer citrate and calcium concentrations. In some embodiments, the mathematical model is used to yield a preliminary predicted post-dialysis systemic ionized calcium concentration.

The method of predicting a concentration of systemic concentration of ionized calcium in the blood of the patient after dialysis is an extension of work done by Kozik-Jaromin. J. Kozik-Jaromin, *Citrate kinetics during regional citrate anticoagulation in extracorporeal organ replacement therapy*, Internal Medicine IV, Nephrology 2005. The seven main components of the method are schematically illustrated in FIGS. 1 and 3A, and described below.

Sys. Calculation of systemic citrate (Ci) generation, citrate metabolism, and resulting citrate and calcium equilibria.

a) Ci generation is calculated assuming an average generation rate of 240 mg/24 h.

b) Ci metabolism: $C_{Ci}(t) = C_0 \cdot e^{-k \cdot t}$ with k=0.0145 min−1 c) Solute equilibria ($Ca^{++}$, protein bound Ca, free Ci, CaCi complexes) are calculated assuming a mono-ionic milieu, using the following dissociation constants: $K_{CaCi}$ (for CaCi complexes)=0.776 mmol/L; $K_{CaP}$ (for Ca-protein binding)=11 mmol/L.

1. Calculation of citrate and calcium concentration changes caused by access recirculation.

2. Calculation of pre-dialyzer Ci concentration required to achieve target pre-dialyzer ionized calcium concentration:

a) Concentration of protein binding sites for calcium ($C_B$) according to protein concentration and 12 binding sites per molecule of albumin b) $C_{CiT}[-(C_{Ca++})^3-(C_{Ca++})^2 \cdot K_{CaCi}-(C_{Ca++})^2 \cdot K_{CaP}-(C_{Ca++})^2 \cdot C_B+(C_{Ca++})^2 \cdot C_{CaT}-C_{Ca++} \cdot K_{CaCi} \cdot K_{CaP}-K_{CaCi} \cdot C_B+C_{Ca++} \cdot K_{CaCi} \cdot C_{CaT}+C_{Ca++} \cdot K_{CaP} \cdot C_{CaT}+K_{CaCi} \cdot K_{CaP} \cdot C_{CaT}]/[(C_{Ca++})^2+C_{Ca++} \cdot K_{CaP}]$ J. Calculation of diffusive and convective dialyzer solute fluxes, assuming $KoA_{Ca\_free}$=603 mL/min; $KoA_{Ci\_free}$=337 mL/min; $KoA_{CaCi}$=337 mL/min. See Kozik-Jaromin.

3. Calculation of post-dialyzer solute concentrations according to trans-membrane mass balances and solute distribution volume changes. Calculation of solute equilibria as in step 3, and $C_{Ci\_free} = C_{Ci\_total} - C_{CaCi}$.

4. Calculate solute concentrations post Ca substitution:

a) Total Ca, total Ci, Ca binding sites: self-evident (as per volume expansion)

b) $Ca^{++}$ and CaCi as per calculations in step 3 c) $C_{Ci\_free} = C_{CiT} - C_{CaCi}$

5. Calculation of dialysate composition with respect to free Ci, $Ca^{++}$, CaCi complexes:

a) $C_{Ci\_free} = -0.5 \cdot \sqrt{0.5 \cdot (C_{CaT} - C_{CiT} + K_{CaCi})^2 + K_{CaCi} \cdot C_{CiT}}$ -continued b) $C_{Ca\_free} = C_{CaT}$ OR $\dfrac{K_{CaCi} \cdot (C_{CiT} - C_{Ci\_free})}{C_{Ci\_free}}$ (if citrate – containing dialysate)

c) $C_{CaCi} = \dfrac{C_{Ca\_free} \cdot C_{Ci\_free}}{K_{CaCi}}$

In another embodiment, a method of modeling a concentration of citrate and calcium and dialyzing blood of a patient can include the computer implemented steps of determining a blood flow rate from and back to the patient through an extracorporeal dialysis circuit including a dialyzer having semi-permeable dialysis membranes and a dialysate chamber surrounding the membranes, and determining a flow rate through the dialysate chamber of the dialyzer of a dialysate that includes a predetermined amount of calcium and a predetermined amount of citrate, and computing an amount of citrate to be introduced into the blood, upstream of the dialyzer, such that ionized calcium is reduced upstream of the dialyzer to a concentration that is sufficiently small to reduce clotting of the flowing blood. In one embodiment, the method can include the step of computing the concentration of ionized calcium in the blood of a patient. In another embodiment, the method can include the step of computing the concentration of citrate in the blood of the patient. A flow chart of the computer-implemented modeling method is illustrated in FIG. 3B.

Figure 3B:
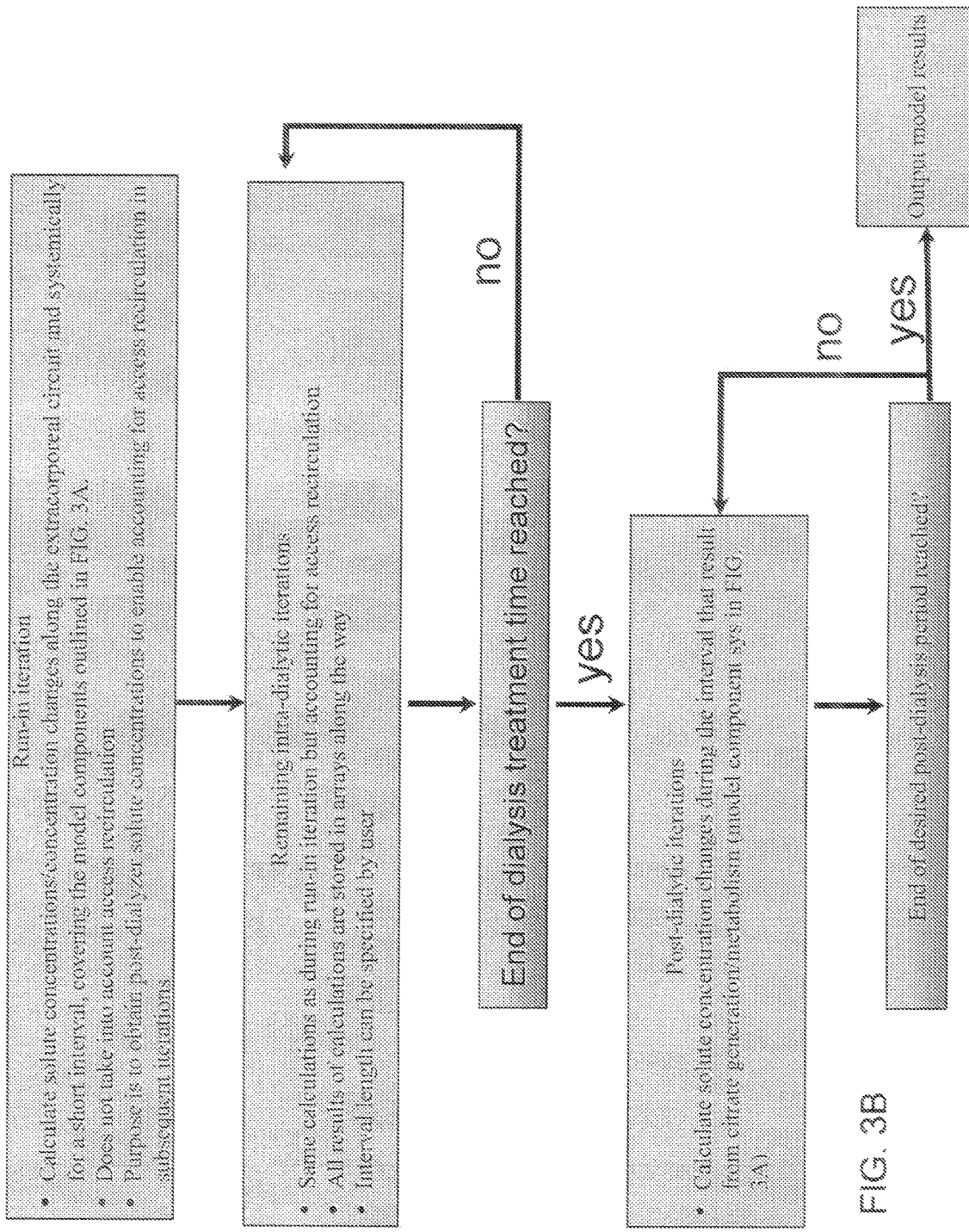
FIG. 3B is a flow chart of a computer implemented mathematical model of predicting a systemic ionized calcium concentration in the blood of the patient according to this invention.

As shown in FIG. 3B, the entire hemodialysis (HD) treatment is modeled iteratively by performing these calculations for consecutive intervals of user-definable (ideally close to infinitesimal) duration.

The distribution volume for calcium and citrate is assumed to be extracellular water, which was approximated in liters as the sum of one third of the urea distribution volume in liters (derived from formal urea kinetic modeling) and the patient's current interdialytic weight gain in kilograms. Urea distribution volume can alternatively be assessed by means of tracer dilution assay, bioelectrical impedance analysis or anthropometric equations.

For each iteration, the amount of total calcium in the extracellular fluid volume (calculated as the product of its concentration and its distribution volume, i.e., extracellular fluid volume) is corrected to reflect the respective transmembrane calcium mass transfer (in all considered chemical forms, and including both diffusive and convective transfer). The resulting total calcium amount in the extracellular fluid volume is then divided by the calcium distribution volume (i.e., extracellular fluid volume) at the end of the interval (taking into account ultrafiltration) to arrive at the systemic total calcium concentration at the end of the interval. An analogous process is followed for citrate and protein concentrations. The systemic ionized calcium concentration is then determined by rearranging the equation in step 2b to solve for ionized calcium concentration (which yields a cubic equation in the normal form) and then solving this cubic equation either iteratively or numerically.

A description of the program code is provided in Tables I and II. The nomenclature for variables used in the program code is as follows: "_sys," "_loc1," "_loc2," "_loc3," "_loc4," and "_loc5" denote the location along the extracorporeal circuit (points sys, 1-5 shown in FIG. 1), and "_beg," and "_end" denote the beginning and end of an iteration interval, respectively. There are three simulation modes: simulation mode 1 (sim1) uses a target pre-filter ionized calcium concentration, then keeps the citrate infusion rate fixed; simulation mode 2 (sim2) uses a target pre-filter ionized calcium concentration, then keeps the pre-filter ionized calcium concentration fixed; and simulation mode 3 (sim3) uses a specified citrate infusion rate profile.

Figure 3C:
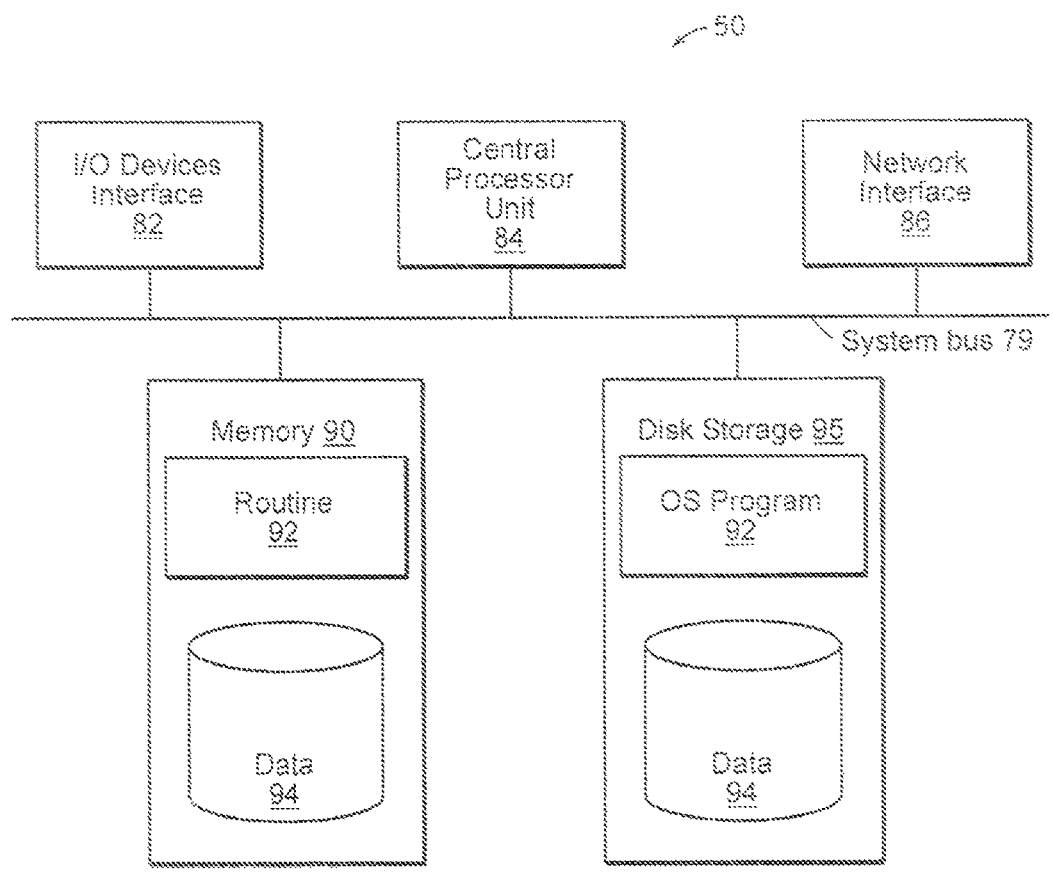
FIG. 3C is a block diagram of a computer apparatus implementing methods of the present invention.

One or more computers 50 execute the program code and may be of a variety of computer architectures such as client-server, standalone processor, networked or distributed processor. FIG. 3C is a diagram of the internal structure of a computer 50 in a computer network or other computer based environment in which the present invention can be implemented. Each computer 50 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the computer 50. Network interface 86 allows the computer to connect to various other devices attached to a network (e.g., global computer network, local area network, wide area network, and the like). Memory 90 provides volatile storage for computer software instructions 92 and data 94 used to implement an embodiment of the present invention (e.g., the mathematical model, process of predicting the concentration of systemic ionized calcium in the blood of the patient, statistical corrector of the preliminary predicted post-dialysis concentration of systemic ionized calcium in the patient's blood, and supporting code detailed above, below, and in Tables I and II). Disk storage 95 provides non-volatile storage for computer software instructions 92 and data 94 used to implement an embodiment of the present invention. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product embodied on a propagated signal on a propagation medium (e.g., a radio wave, an infrared wave, a laser wave, a sound wave, or an electrical wave propagated over a global network such as the Internet, or other network(s)). Such carrier medium or signals provide at least a portion of the software instructions for the present invention routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 is a propagation medium that the computer system 50 may receive and read, such as by receiving the propagation medium and identifying a propagated signal embodied in the propagation medium, as described above for computer program propagated signal product.

Generally speaking, the term "carrier medium" or transient carrier encompasses the foregoing transient signals, propagated signals, propagated medium, storage medium and the like.

Prediction Results

Seventeen hemodialysis treatments were conducted on 8 maintenance HD patients using citrate bicarbonate dialysate (Citrasate® dialysate, Advanced Renal Technologies, Bellevue, Wash.; 3 mEq/L calcium, 2.4 mEq/L citrate). For one treatment only, Citrasate with 2.5 mEq/L Ca was used. No post-dialyzer Ca infusion was performed. Total Ca, $Ca^{++}$ and total Ci were measured systemically, pre- and post-dialyzer at the following time points: before HD (systemically only), at several time points throughout the treatment, and at the end of HD. The measurements of systemic Ca, $Ca^{++}$ and total Ci were taken from the arterial line, upstream of the citrate infusion port while the blood flow rate was reduced to about 50 mL/min. Total protein and albumin were measured before dialysis. The most recent alkaline phosphatase (AP) and total parathyroid hormone (PTH) (Scantibodies assay, Scantibodies Laboratory, Inc., Santee, Calif.) were recorded. Trisodium citrate (136 mmol/L; 4%) was infused into the arterial line at various rates to result in pre-dialyzer Ca values of approx. 0.25 to 0.65 mmol/L. Blood flow rate was 350 mL/min in 4 treatments and 400 mL/min in 13 treatments; the dialysate flow rate was fixed at 500 mL/min. All subjects used Optiflux F180NR dialyzers (Fresenius Medical Care North America, Waltham, Mass.).

Measured and predicted systemic $Ca^{++}$ were compared pre-HD and at 15 min into the treatment. For the latter, pre-HD predicted were adjusted to measured values. Pre- and post-dialyzer comparisons between measured and estimated $Ca^{++}$ were performed at 15 min into the treatment. Deviations between predicted and measured systemic $Ca^{++}$ over the entire treatment were compared for tertiles of AP and tPTH.

Results are presented below as mean±standard deviation (SD) unless otherwise noted. Differences between predicted and measured values were calculated as predicted minus measured and were tested for significant deviation from zero by means of two-tailed one-sample t test. Bland-Altman plots were generated and the underlying data analyzed for systematic bias by means of linear regression. Statistical significance was accepted for an alpha level of <0.05.

The study cohort consisted of 8 subjects (age 63±13.6 years, 4 males). Measured and predicted systemic $Ca^{++}$ [mmol/L] at baseline (pre-HD) was 1.08±0.06 and 1.05±0.05, respectively (difference −0.03±0.046, 95% CI −0.055 to −0.007; FIG. 4A), and at 15 min into the treatment 1.01±0.05 and 1.02±0.05, respectively (difference 0.012±0.054, 95% CI −0.015 to 0.4; FIG. 4B). At 15 min, the measured and predicted pre-dialyzer Ca was 0.33±0.06 and 0.39±0.05, respectively (difference 0.06±0.03, 95% CI 0.044 to 0.077; FIG. 4C). At the same time point, corresponding post-dialyzer Ca was 0.7±0.05 and 0.61±0.05, respectively (difference −0.09±0.04, 95% CI −0.11 to −0.07; FIG. 4D). Neither visual inspection of Bland-Altman plots nor formal analysis of the underlying data revealed any systematic bias in any of these predictions.

Figure 5:
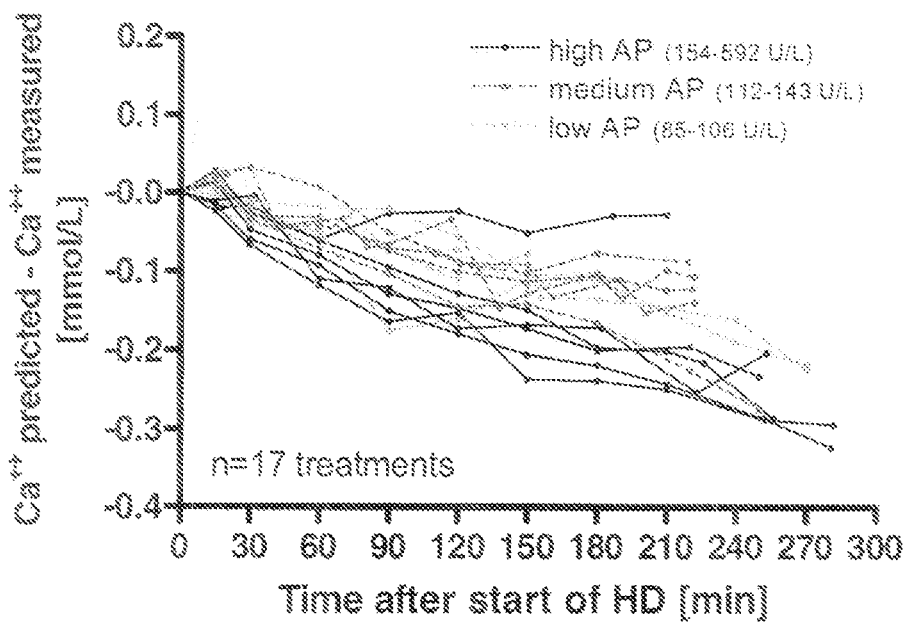
FIGS. 5A-B are graphs of predicted systemic iCa (mmol/L) minus measured systemic iCa as a function of time (minutes) after start of hemodialysis for seventeen dialysis treatments on patients.
Figure 5:
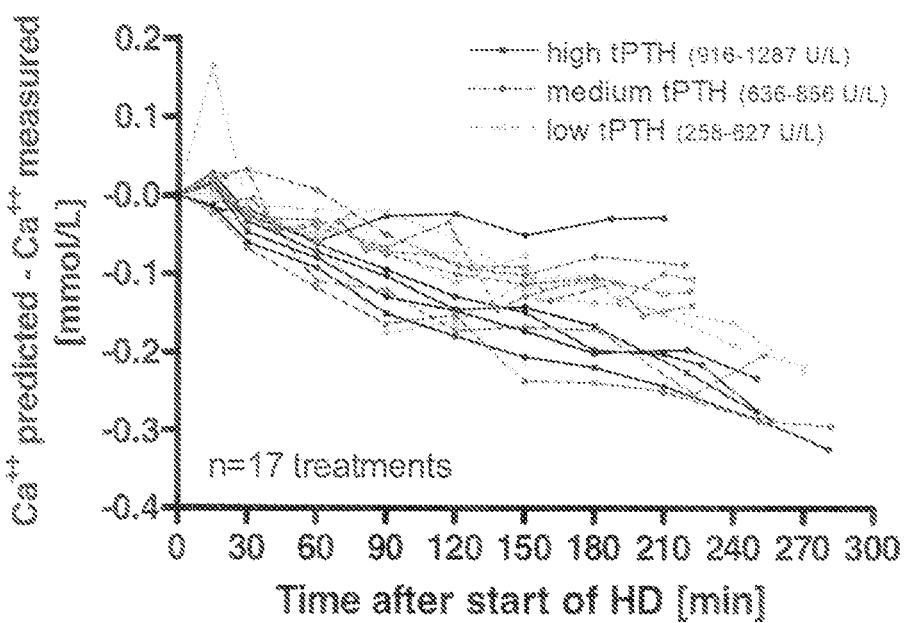

The tertile ranges for AP were 85 to 106 U/L (low AP), 112 to 143 U/L (medium AP), and 154 to 592 U/L (high AP). For PTH, the tertile ranges were 258 to 627 pg/mL (low PTH), 636 to 856 pg/mL (medium PTH), and 916 to 1287 pg/mL (high PTH). FIG. 5 shows the difference between predicted and measured systemic $Ca^{++}$ plotted against treatment time. FIG. 5A is stratified by AP tertiles; FIG. 5B is stratified by PTH tertiles. While the curves for the low and medium tertiles show no clear separation, the curves corresponding to the high AP tertile as well as the high tPTH tertile cluster toward the bottom of the plots, indicating that the most pronounced differences between predicted and measured values occur in these tertiles.

Multiple Linear Regression Model

Additionally, the method can further include statistically correcting the preliminary predicted post-dialysis concentration of systemic ionized calcium in the patient's blood to provide a final predicted post-dialysis systemic ionized calcium concentration. Statistically correcting the preliminary predicted post-dialysis concentration of systemic ionized calcium in the patient's blood can include classifying the patient's parathyroid hormone (PTH) level or alkaline phosphatase (AP) level into at least two categories of PTH or AP levels based on concentration, and estimating a difference between the preliminary predicted and the actual post-dialysis concentration of systemic ionized calcium in the patient's blood based on the category of the PTH or AP level of the patient, dialysis treatment time, and the preliminary predicted post-dialysis concentration of systemic ionized calcium, thereby obtaining a correction to the preliminary predicted post-dialysis concentration of systemic ionized calcium in the patient's blood. The difference between the preliminary predicted and actual post-dialysis concentration of systemic ionized calcium in the patient's blood can be determined by employing a multivariate linear regression model including the category of the PTH or AP level of the patient, dialysis treatment time, and the preliminary predicted concentration of systemic ionized calcium in the patient's blood. The PTH or the AP level in the patient's blood can be classified into categories, for example, tertiles, quartiles, quintiles, etc.

The predicted results discussed above (denoted as preliminary predicted results in this section) in a cohort of 8 patients (17 treatments) demonstrated an underestimation of post-dialysis systemic iCa in the range of 0.03 to 0.29 mmol/L (average 0.15 mmol/L, 95% confidence interval, CI, 0.11 to 0.20 mmol/L). Furthermore, it was shown above that the accuracy of prediction relates to the individual subject's parathyroid hormone (PTH) and alkaline phosphatase (AP) levels. Without wishing to be bound to any particular theory, it is believed that these levels are surrogate markers of bone turnover and, hence, calcium buffering capacity. It will be shown below that the difference between end-dialysis systemic iCa estimated by the method described above and the measured end-dialysis systemic iCa also relates to the duration of the hemodialysis treatment and to the predicted post-dialysis systemic iCa.

Determining a model concentration of systemic ionized calcium in the patient's blood after dialysis includes employing a statistical multivariate linear regression model to determine the difference ($\Delta iCa_{pred\_MLR}$) between the predicted end-dialysis systemic iCa obtained by the method described above ($iCa_{pred\_RCA}$), and the actual, measured, end-dialysis systemic iCa ($iCa_{actual}$). This difference, $\Delta iCa_{pred\_MLR}$, can then be used to correct the estimated value and yield an accurate model end-dialysis systemic iCa prediction ($iCa_{pred\_hybrid}$). The mathematical relationships used in applying the model are as follows:

$$\Delta iCa_{pred\_MLR} = iCa_{pred\_RCA} - iCa_{actual} \qquad (i)$$

$$iCa_{pred\_hybrid} = iCa_{pred\_RCA} - \Delta iCa_{pred\_MLR} \qquad (ii)$$

The multivariate regression model can use as many parameters as can be validated to predict the difference between the estimated systemic iCa ($iCa_{pred\_RCA}$) and the actual iCa ($iCa_{actual}$). This number of predictors is likely to increase as the number of available data points for model generation increases, and can comprise any variables that can be shown to relate to the prediction accuracy of the estimation method described above, including (without limitation) PTH level, AP level, the duration of the hemodialysis treatment, the subject's age, race, gender, average citrate infusion rate, urea distribution volume, extracellular fluid volume, pre-dialysis total or ionized calcium, phosphate binder therapy, cinacalcet medication, vitamin D or VDRA therapy, serum phosphorus, serum albumin, hematocrit, blood flow rate, and the predicted iCa result itself. As described below, preferred variables are, first, the set of PTH level, hemodialysis treatment time, and the predicted iCa result, and, second, the set of AP level, hemodialysis treatment time, and the predicted iCa result. Continuous parameters may be entered as scale variables or in categorized form, that is, classified into categories of increasing amounts of a variable. The number of categories can be at least two categories, such as, for example, tertiles, quartiles, or quintiles.

Results of Multiple Linear Regression Model

The following analyses were performed in a cohort of 8 subjects (17 treatments). $\Delta iCa_{pred\_RCA}$ denotes the difference between the end-dialysis iCa as predicted by the method described above and the actual (measured) end-dialysis iCa, with $$\Delta iCa_{pred\_RCA} = iCa_{pred\_RCA} - iCa_{actual} \quad \text{(iii)}$$

Bi-variate correlation analysis revealed associations between $\Delta iCa_{pred\_RCA}$ and tertiles of PTH (PTH_tertile), tertiles of AP (AP_tertile), duration of hemodialysis treatment ($t_d$), and $iCa_{pred\_RCA}$ (as shown below in Table 1; all significant, except borderline significance for PTH tertiles).

TABLE 1

Bivariate correlations for variables used in subsequent multivariate model construction

|  |  | PTH_tertile | AP_tertile | td | $iCa_{pred\_RCA}$ |
|---|---|---|---|---|---|
| $\Delta iCa_{pred\_RCA}$ | Pearson Correlation | −0.412 | −.514(*) | −.656() | .828() |
|  | Sig. (2-tailed) | 0.100 | 0.035 | 0.004 | 0.000 |
|  | N | 17 | 17 | 17 | 17 |

*Correlation is significant at the 0.05 level (2-tailed).
**Correlation is significant at the 0.01 level (2-tailed).

A multiple linear regression model (MLR1) was fitted with $\Delta iCa_{pred\_RCA}$ as the dependent variable and PTH_tertile, $t_d$, and $iCa_{pred\_RCA}$ as predictors. Tables 2 and 3 below show the respective model statistics.

TABLE 2

Analysis of variance (ANOVA) for model MLR1 [a], [b]

| Model |  | Sum of Squares | df | Mean Square | F | Sig. |
|---|---|---|---|---|---|---|
| MLR1 | Regression | 0.082 | 3 | 0.027 | 11.880 | .001 |
|  | Residual | 0.030 | 13 | 0.002 |  |  |
|  | Total | 0.112 | 16 |  |  |  |

[a] Predictors: (Constant), PTH_tertile, td, $iCa_{pred\_RCA}$
[b] Dependent Variable: $\Delta iCa_{pred\_RCA}$

TABLE 3

Model coefficients for model MLR1 (Dependent variable: $\Delta iCa_{pred\_RCA}$)

|  |  | Unstandardized Coefficients | | Standardized Coefficients | | |
|---|---|---|---|---|---|---|
| Model |  | B | Std. Error | Beta | t | Sig. |
| MLR1 | (Constant) | −0.5861999002 | 0.171 |  | −3.433 | 0.004 |
|  | td | −0.0003737443 | 0.000 | −0.277 | −1.509 | 0.155 |
|  | $iCa_{pred\_RCA}$ | 0.5895283578 | 0.157 | 0.689 | 3.751 | 0.002 |
|  | PTH_tertile | 0.0047472376 | 0.017 | 0.047 | 0.277 | 0.786 |

As an example of the use of model coefficients for a given patient, $\Delta iCa_{pred\_RCA}$ can be obtained from the coefficients in Table 3 by $$\Delta iCa_{pred\_RCA} = -0.5861999002 - 0.0003737443 * t_d + 0.5895283578 * iCa_{pred\_RCA} + + 0.0047472376 * PTH\_tertile \quad \text{(Example)}$$

where the patient's treatment time, RCA model prediction of systemic ionized calcium, and PTH tertile are substituted into the equation to yield the correction term for the patient. The coefficients are subject to change for example, for a larger set of patient data, or a different number of categories of PTH levels.

Another multiple linear regression model (MLR2) was fitted with $\Delta iCa_{pred\_RCA}$ as the dependent variable and AP_tertile, $t_d$, and $iCa_{pred\_RCA}$ as predictors. Tables 4 and 5 show the respective model statistics.

TABLE 4

Analysis of variance (ANOVA) for model MLR2 [a], [b]

| Model | | Sum of Squares | df | Mean Square | F | Sig. |
|---|---|---|---|---|---|---|
| MLR2 | Regression | 0.082 | 3 | 0.027 | 11.806 | .001 |
| | Residual | 0.030 | 13 | 0.002 | | |
| | Total | 0.112 | 16 | | | |

[a] Predictors: (Constant), AP_tertile, td, $iCa_{pred\_RCA}$
[b] Dependent Variable: $\Delta iCa_{pred\_RCA}$

TABLE 5

Model coefficients for model MLR2 (Dependent Variable: $\Delta iCa_{pred\_RCA}$)

| Model | | Unstandardized Coefficients | | Standardized Coefficients | | |
|---|---|---|---|---|---|---|
| | | B | Std. Error | Beta | t | Sig. |
| 1 | (Constant) | -0.5613273965 | 0.176 | | -3.192 | 0.007 |
| | TIME | -0.0003456055 | 0.000 | -0.256 | -1.386 | 0.189 |
| | $iCa_{pred\,RCA}$ | 0.5700463766 | 0.161 | 0.666 | 3.536 | 0.004 |
| | AP_tertile | -0.0023451955 | 0.018 | -0.023 | -0.130 | 0.899 |

These regression models were used (separately) to estimate the difference ($\Delta iCa_{pred\_MLR}$) between the predicted end-dialysis systemic iCa ($iCa_{pred\_RCA}$) and the actual (measured) end-dialysis systemic iCa ($iCa_{actual}$). $\Delta iCa_{pred\_MLR}$ was then used for simple additive correction of $iCa_{pred\_RCA}$ to yield the final corrected end-dialysis systemic iCa model prediction ($iCa_{pred\_hybrid}$). Equation (ii) applies accordingly.

Figure 6:
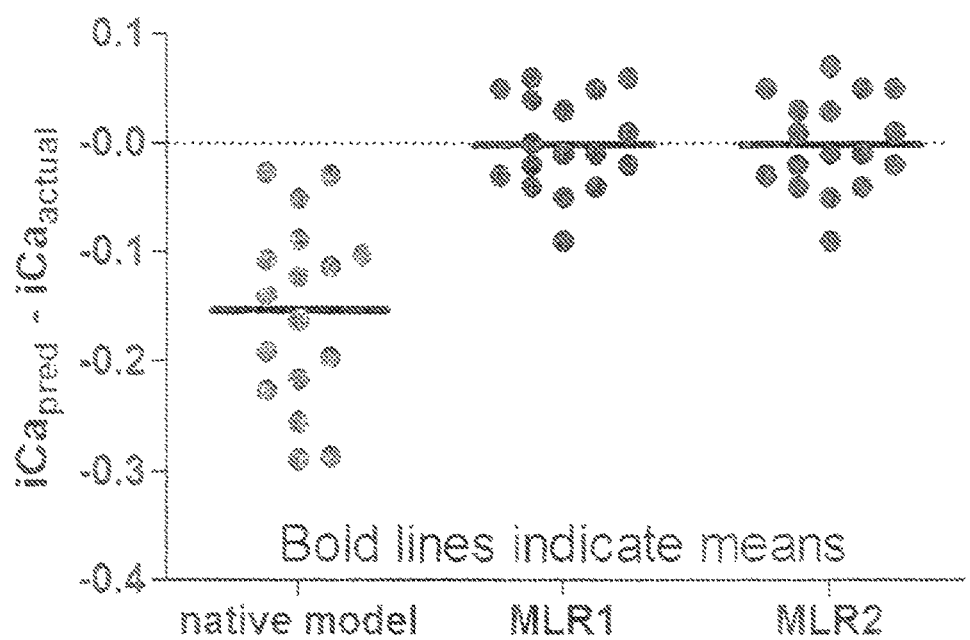
FIG. 6 is a graph of predicted systemic iCa minus actual (measured) systemic iCa at the end of 17 hemodialysis treatments on patients comparing the prediction accuracy for the native model and two models employing multivariate linear regression (MLR1 and MLR2). Bold lines indicate the means for the models. The thin dashed line indicates zero difference between the predicted and measured end-dialysis systemic iCa.

FIG. 6 shows a comparison of the post-dialysis systemic iCa prediction accuracy of the method described above and the two described realizations of the new model (MLR1 and MLR2, respectively). As shown in FIG. 6, the prediction using the method described above yields an underestimation of actual iCa in the range of 0.03 to 0.29 mmol/L with an average $\Delta iCa_{pred\_RCA}$ of -0.15 mmol/L (95% confidence interval, CI, -0.20 to -0.11 mmol/L). In contrast, when either of the models is used (MLR1 or MLR2), there is on average no difference between the model prediction and the measured iCa (for both models: $\Delta iCa_{pred\_hybrid} = -0.0006$ mmol/L, 95% CI -0.023 to 0.022 mmol/L; not significantly different from zero, P=0.96, one sample t test). Therefore, the described model significantly improves the prediction of end-dialysis systemic iCa in regional citrate anticoagulation.

Figure 7:
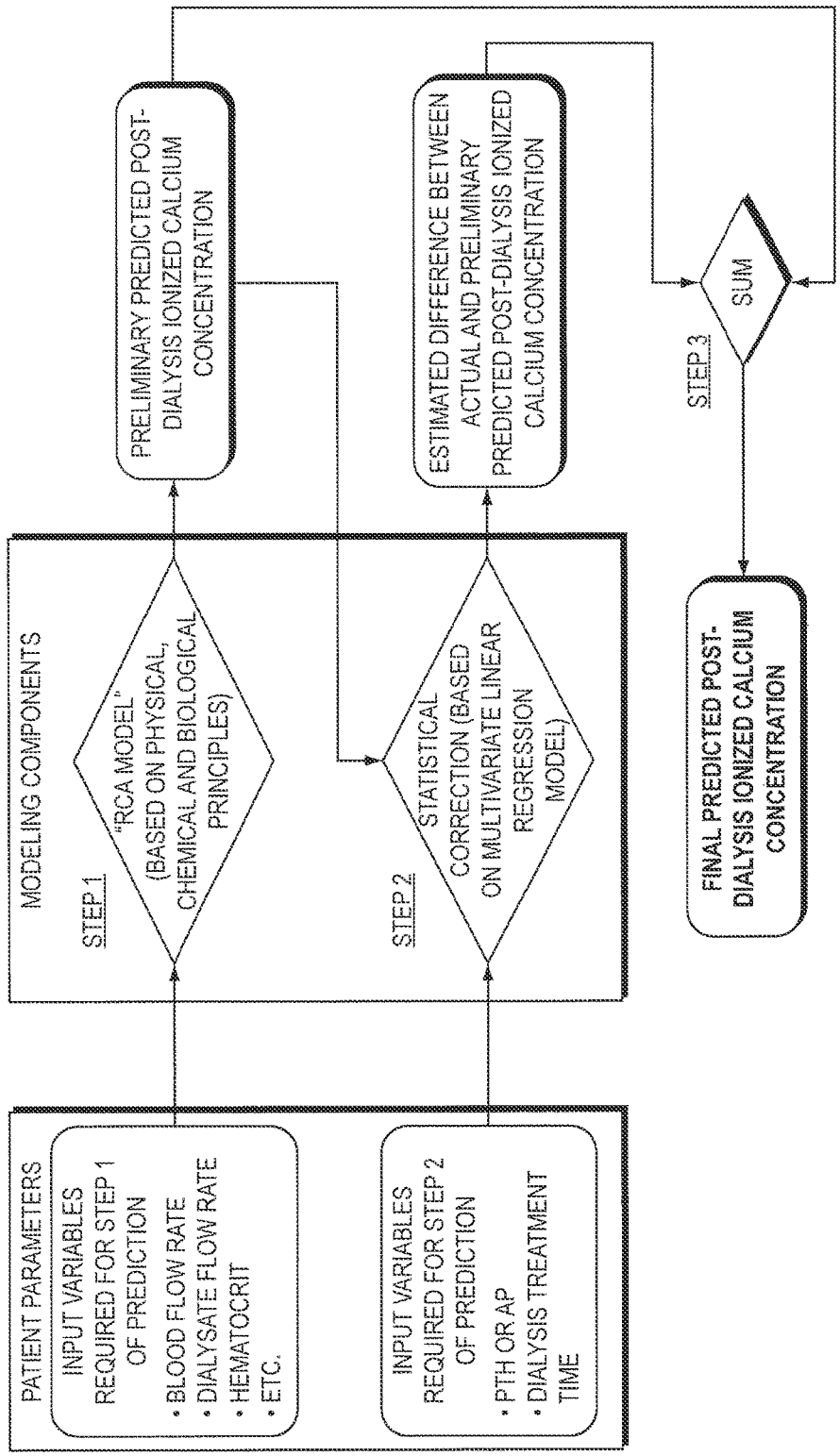
FIG. 7 is a flow chart of predicting the post-dialysis systemic ionized calcium concentration for a patient employing a statistical correction based on the category of the PTH or AP level of the patient, dialysis treatment time, and the preliminary predicted post-dialysis concentration of systemic ionized calcium by the methods of the invention.

FIG. 7 shows a flow chart for predicting post-dialysis systemic ionized calcium concentration for a patient using the methods described above.

In another embodiment, the method can further include statistically correcting the preliminary predicted concentration of systemic ionized calcium in the patient's blood at any time point during dialysis to provide a final predicted systemic ionized calcium concentration for that time point. Statistically correcting the preliminary predicted concentration of systemic ionized calcium in the patient's blood at any time point during dialysis can include classifying the patient's parathyroid hormone (PTH) level or alkaline phosphatase (AP) level into at least two categories of PTH or AP levels based on concentration, and estimating a slope ("prediction error slope") of the relationship between the prediction error of the preliminary systemic ionized calcium concentration in the patient's blood and the elapsed time of dialysis, based on the category of the PTH or AP level of the patient and the preliminary predicted post-dialysis concentration of systemic ionized calcium. The prediction error slope can be determined by employing a multivariate linear regression model including the category of the PTH or AP level of the patient and the preliminary predicted post-dialysis concentration of systemic ionized calcium in the patient's blood as independent variables. The PTH or the AP level in the patient's blood can be classified into categories, for example, tertiles, quartiles, quintiles, etc.

Figure 8:
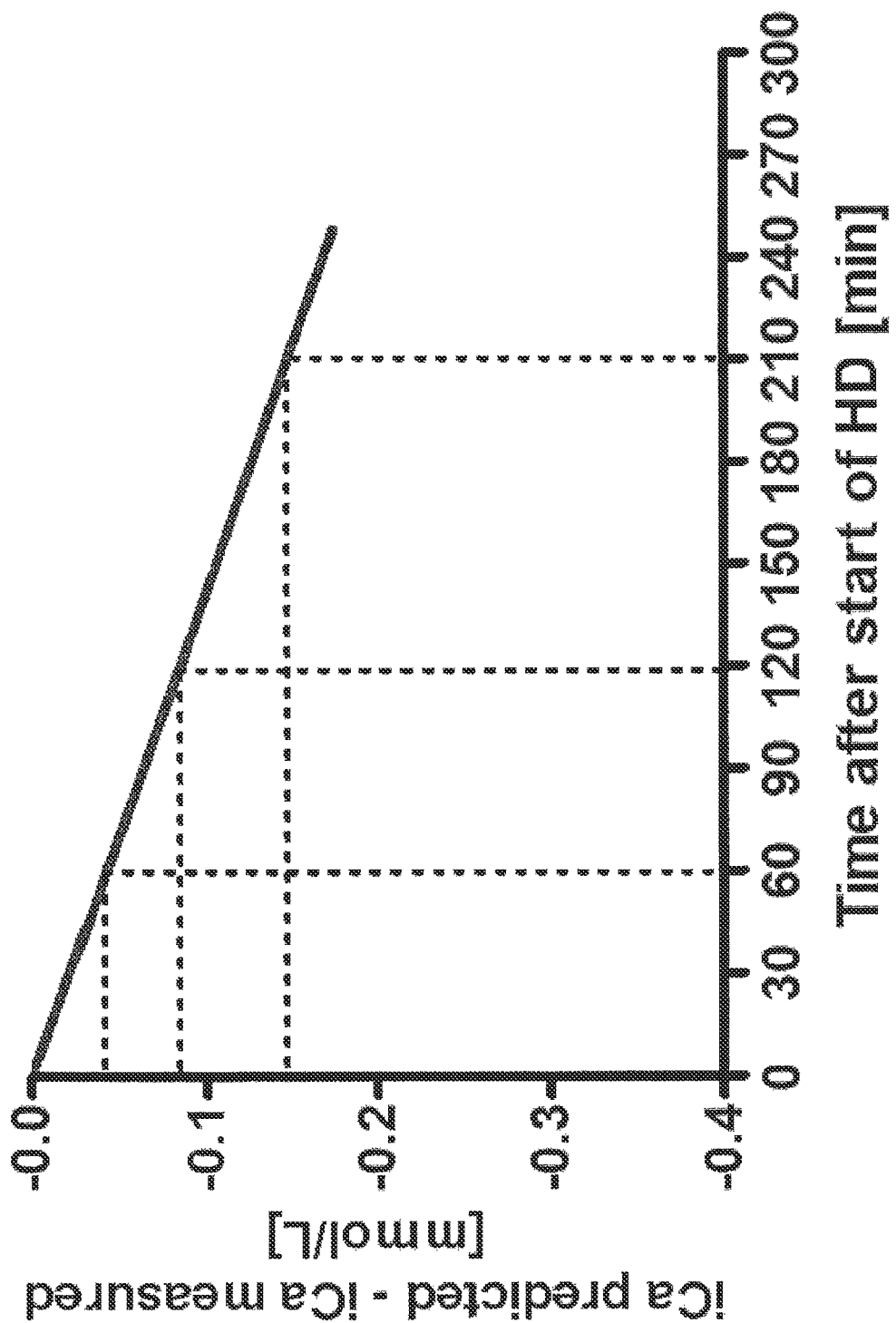
FIG. 8 is a graph of a hypothetical example of the slope of the relationship between the prediction error (preliminary predicted systemic iCa minus actual measured systemic iCa) and elapsed time of dialysis, which is used to estimate the expected prediction error for any time point during the treatment.
Figure 9:
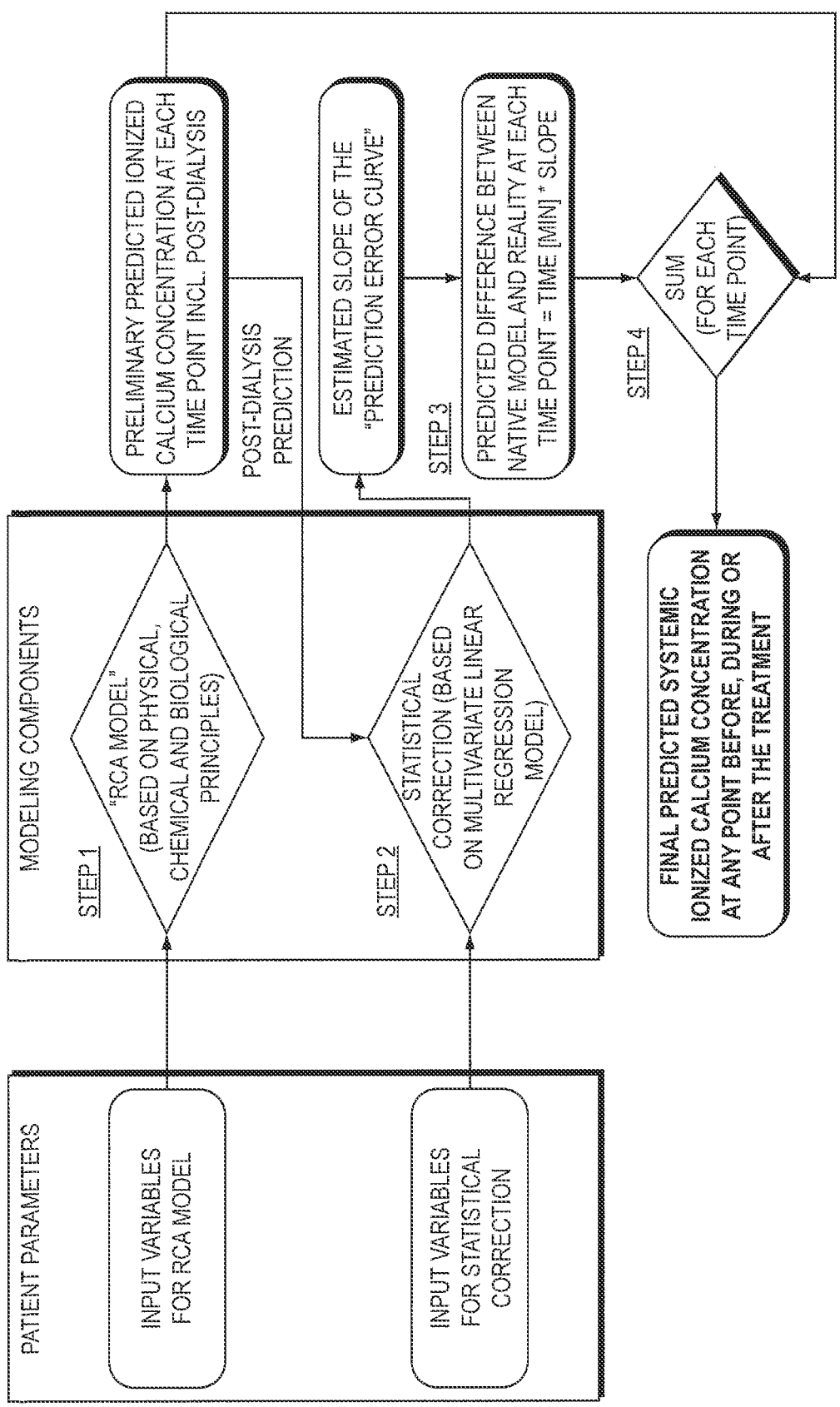
FIG. 9 is a flow chart of predicting the post-dialysis systemic ionized calcium concentration for a patient employing a statistical correction based on the category of the PTH or AP level of the patient and the preliminary predicted post-dialysis concentration of systemic ionized calcium by the methods of the invention.

Determining a model concentration of systemic ionized calcium in the patient's blood at any given time point during dialysis includes employing a statistical multivariate linear regression model to determine this prediction error slope and multiplying it by the elapsed time of dialysis at the time point of interest, thereby obtaining an estimated prediction error for the preliminary predicted systemic ionized calcium concentration in the patient's blood at that time point (illustrated in FIG. 8). This estimated prediction error can then be used to correct the preliminary estimated value and yield an accurate model systemic ionized calcium prediction for that time point (see FIG. 9 for a flowchart of this process).

As was shown above in FIGS. 5A and 5B, the relationship between the prediction error of the preliminary ionized calcium concentration in the patient's blood and the elapsed time of dialysis is near-linear. The following analyses were performed in a cohort of 8 subjects (17 treatments). For each treatment, a linear regression slope was calculated for the relationship between the prediction error of the preliminary systemic ionized calcium concentration in the patient's blood and the elapsed time of dialysis (hereafter referred to as "slope"), and the preliminary predicted post-dialysis systemic ionized calcium concentration in the patients' blood was obtained. PTH values for all treatments were categorized into tertiles. A multiple linear regression (MLR) model was constructed using slope as dependent variable and preliminary predicted post-dialysis systemic iCa concentration and PTH category as independent variables. The MLR model yielded an overall significance level of P=0.018, as shown in Table 6, along with the overall model statistics for multiple linear regression model using prediction error slope as dependent variable and tPTH tertiles and preliminary predicted end-dialysis systemic ionized calcium concentration as independent variables.

TABLE 6

Overall model statistics for MLR model using tPTH tertile and RCA model prediction

| Model | | Sum of Squares | df | Mean Square | F | Sig. |
|---|---|---|---|---|---|---|
| 1 | Regression | .000 | 2 | .000 | 5.474 | .018(a) |
|   | Residual | .000 | 14 | .000 | | |
|   | Total | .000 | 16 | | | |

(a)Predictors: (Constant), ICA_PRED, TPTH_3TI
b Dependent Variable: SLOPE

The parameter estimates are given in Table 7. The linear equation derived for slope estimation was found to be:

slope=−0.0025726570+8.86644·10$^{-5}$·tPTH tertile+ 0.0018663110··preliminary systemic end-dialysis ionized calcium prediction     (A)

Table 7 shows the parameter estimates from multiple linear regression model using prediction error slope as dependent variable and tPTH tertiles ("TPTH_3TI") and preliminary predicted end-dialysis systemic ionized calcium concentration ("ICA_PRED") as independent variables.

TABLE 7

Parameter estimates for MLR model using tPTH and RCA model prediction

| | | Unstandardized Coefficients | | Standardized Coefficients | | |
|---|---|---|---|---|---|---|
| Model | | B | Std. Error | Beta | t | Sig. |
| 1 | (Constant) | −.0025726570 | .001 | | −4.633 | .000 |
|   | TPTH_3TI | 8.866440543E−05 | .000 | .302 | 1.325 | .206 |
|   | ICA_PRED | .0018663110 | .001 | .751 | 3.297 | .005 | a Dependent Variable: SLOPE

Figure 10:
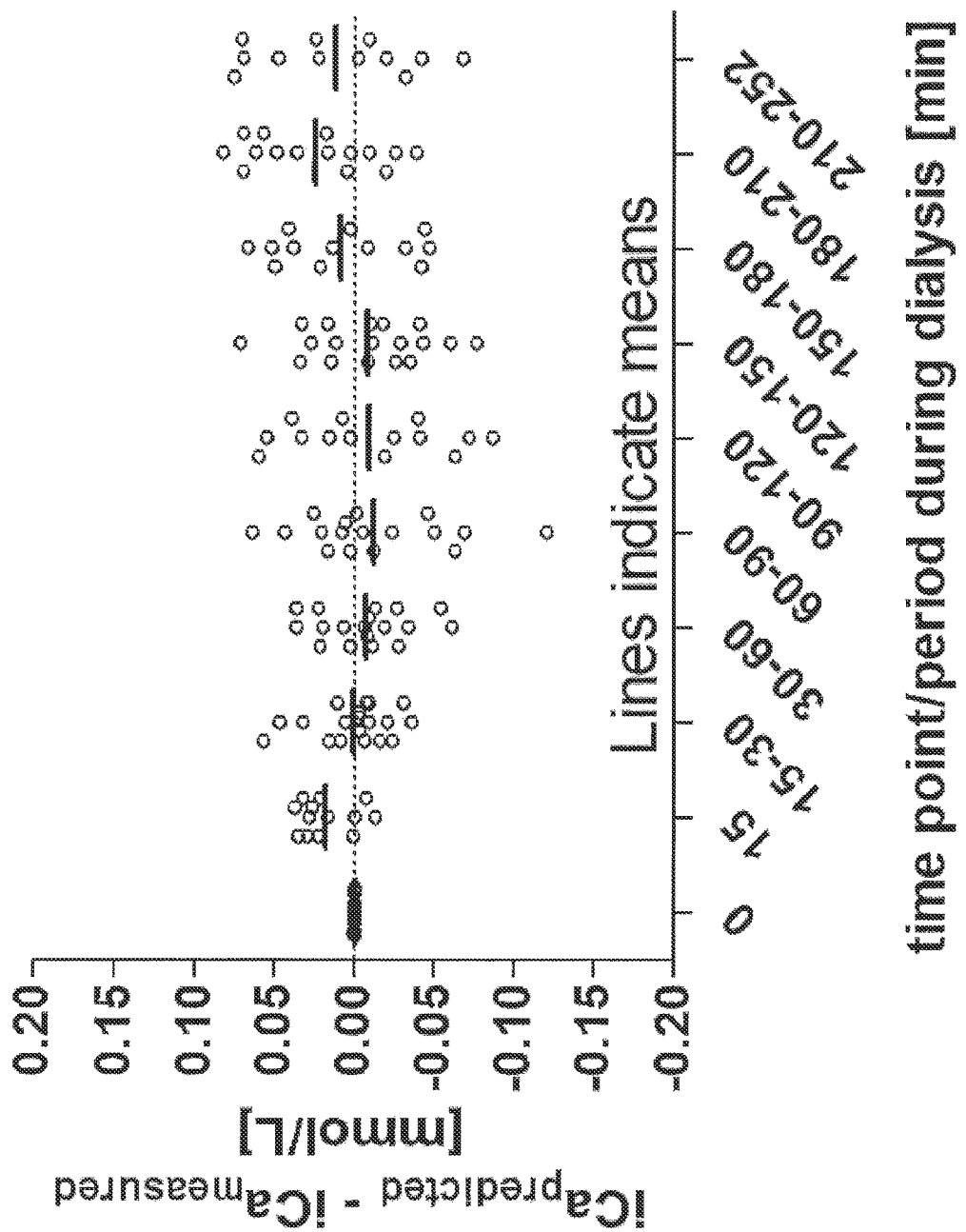
FIG. 10 is a graph of predicted systemic iCa minus actual (measured) systemic iCa as a function of categories of elapsed treatment time during dialysis obtained by the model illustrated in FIG. 9.

Slopes for each treatment were estimated using Eq. A and used to correct the preliminary predicted systemic ionized calcium concentration in the patients' blood for multiple time points during the treatments. From these corrected predictions, the actual measured values for these time points were subtracted to obtain the actual final prediction error, which is shown in FIG. 10. FIG. 10 is an illustration of the prediction error obtained using the slope hybrid model (model-predicted systemic ionized calcium concentration minus actual measured systemic ionized calcium concentration) as a function of categories of elapsed treatment time. As can be seen, the systemic ionized calcium concentration in the patients' blood can be estimated with this slope hybrid model within an error margin of about ±0.1 mmol/L, and this error margin remains stable throughout the entire treatment.

In some embodiments, the method can be employed during dialysis treatment of a patient and include the steps of maintaining or adjusting the patient's intradialytic calcium mass balance to desired levels relative to the patient's interdialytic intakes of calcium during a time in which the patient is undergoing dialysis treatment using a dialyzer that includes a dialysate containing a calcium concentration by determining a desired intradialytic calcium mass balance for the patient over a complete dialysis cycle, calculating an intradialytic calcium mass balance, and adjusting the amount of the citrate to be introduced into the blood. In these embodiments, the method can include the step of adjusting the amount of ionized calcium in the dialysate, as described in application Ser. No. 12/580,803, filed on Oct. 16, 2009, and optionally can include the step of adjusting the amount of citrate in the dialysate.

In yet another embodiment, the computer implemented method of modeling can be used to compute the effects of varying degrees of dialyzer clotting (impairment) on citrate and calcium profiles and mass balances. The method of modeling a concentration of citrate and calcium in dialyzing blood of a patient includes the computer implemented steps of determining a blood flow rate from and back to the patient through an extracorporeal dialysis circuit including a dialyzer having semi-permeable dialysis membranes and a dialysate chamber surrounding the membranes, determining a flow rate through the dialysate chamber of the dialyzer of a dialysate that includes a predetermined amount of calcium and a predetermined amount of citrate, and computing an amount of citrate anticoagulant to be introduced into the blood, upstream of the dialyzer, such that ionized calcium is reduced upstream of the dialyzer to a concentration that is sufficiently small to reduce clotting of the flowing blood.

The method can further include computing a serum concentration of ionized calcium in the blood of the patient, and computing a concentration of citrate in the blood of the patient. In some embodiments, computing the amount of citrate anticoagulant to be introduced includes computationally determining for a given patient certain time periods when the amount of citrate is to be modulated downwardly, and alternating time periods when the amount of citrate is to be modulated upwardly. In certain embodiments, the method is employed during dialysis treatment of a patient.

In still another embodiment, the computer implemented method of modeling can be used to dynamically adjust the citrate flow rate and blood flow rate in order to react to venous pressure changes or hypotensive episodes of the patient, while maintaining a desired pre-dialyzer iCa level.

TABLE I

Explanation of variables used in program code excerpt

RANGES FOR INPUT PARAMETERS

| | |
|---|---|
| rng_Ci_infusion | Worksheet range for citrate infusion rate profile |
| rng_Ca_infusion | Worksheet range for calcium infusion rate profile |
| rng_UFR | Worksheet range for ultrafiltration rate profile |
| rng_C_Ci_infusion | Worksheet range for concentration of citrate infusion |
| rng_C_Ca_infusion | Worksheet range for concentration of calcium infusion |
| rng_Qb | Worksheet range for blood flow rate |
| rng_Qd | Worksheet range for dialysate flow rate |
| rng_recirc_access | Worksheet range for access recirculation |
| rng_Vurea | Worksheet range for Urea distribution volume |
| rng_td | Worksheet range for dialysis treatment time |
| rng_tpost | Worksheet range for duration of post-dialysis period to be modeled |
| rng_C_CaT_loc5 | Worksheet range for dialysate inlet total calcium concentration |
| rng_C_CiT_loc5 | Worksheet range for dialysate inlet total citrate concentration |
| rng_wtgain | Worksheet range for current interdialytic weight gain |
| rng_KMP | Worksheet range for miscible calcium pool buffer coefficient |
| rng_Hct_sys | Worksheet range for systemic hematocrit |
| rng_C_CiT_sys_beg | Worksheet range for systemic total citrate concentration |
| rng_C_CaT_sys_beg | Worksheet range for systemic total calcium concentration |
| rng_C_prot_sys_beg | Worksheet range for systemic protein concentration |
| rng_C_Cafree_loc2 | Worksheet range for pre-filter ionized calcium |
| rng_sel_sim_mode | Worksheet range for specifying the desired simulation mode |

RANGES FOR INTERNAL PARAMETERS

| | |
|---|---|
| rng_gs_iCa | Worksheet range for goal seek cell: iCa concentration |
| rng_gs_K_CaCi | Worksheet range for goal seek cell: CaCi dissociation constant |
| rng_gs_K_CaP | Worksheet range for goal seek cell: CaP dissociation constant |
| rng_gs_C_CiT | Worksheet range for goal seek cell: total citrate concentration |
| rng_gs_C_bindingsites | Worksheet range for goal seek cell: concentration of Ca binding sites |
| rng_gs_C_CaT | Worksheet range for goal seek cell: total calcium concentration |
| rng_gs_cubic | Worksheet range for goal seek cell: cubic equation |

RANGES FOR CONTROL PANEL PARAM.

| | |
|---|---|
| rng_sel_skip_Ci_infusion_iteration | Worksheet range for switch indicating whether or not to skip iterative process to determine the accurate citrate infusion rate |
| rng_K_CaCi | Worksheet range for calcium-citrate complex dissociation constant |
| rng_K_CaP | Worksheet range for calcium-protein dissociation constant |
| rng_KoA_CaCi | Worksheet range for mass transfer area coefficient for CaCi |
| rng_KoA_Cifree | Worksheet range for mass transfer area coefficient for free citrate |
| rng_KoA_Cafree | Worksheet range for mass transfer area coefficient for free calcium |
| rng_k_Ci | Worksheet range for metabolic rate constant for citrate |
| rng_Rate_G_Ci | Worksheet range for citrate generation rate |
| rng_interval_intra | Worksheet range for duration of intradialytic iteration interval |
| rng_interval_post | Worksheet range for duration of postdialytic iteration interval |
| rng_reduction_step | Worksheet range for magnitude of reductions in citrate infusion rate during iterative process to find accurate infusion rate |
| rng_sel_use_iCa_tolerance | Worksheet range for switch indicating whether or not to allow for iCa tolerance when iterating to find accurate citrate infusion rate |
| rng_tolerance_Cafree_loc2 | Worksheet range for magnitude of iCa tolerance when iterating to find accurate citrate infusion rate |

INPUT VARIABLES FROM CONTROL PANEL (switches, selections, constants)

| | |
|---|---|
| sel_skip_Ci_infusion_iteration | Switch that determines whether or not to skip the iterative process determining the accurate citrate infusion rate required to reach the pre-filter iCa target |
| sel_sim_mode | Simulation mode |
| reduction_step | Magnitude of reductions in citrate infusion rate during iterative process to find accurate infusion rate |
| sel_use_iCa_tolerance | Switch indicating whether or not to allow for iCa tolerance when iterating to find accurate citrate infusion rate |
| tolerance_Cafree_loc2 | Magnitude of iCa tolerance when iterating to find accurate citrate infusion rate |
| K_CaCi | Calcium-citrate complex dissociation constant [mmol/L] (e.g., 0.776 mmol/L) |
| K_CaP | Calcium-protein dissociation constant [mmol/L] (e.g., 11 mmol/L) |
| KoA_CaCi | Dialyzer mass transfer area coefficient for CaCi [L/min] (e.g., 0.337 L/min) |
| KoA_Cifree | Dialyzer mass transfer area coefficient for free citrate [L/min] (e.g., 0.337 L/min) |
| KoA_Cafree | Dialyzer mass transfer area coefficient for free calcium [L/min] (e.g., 0.603 L/min) |
| k_Ci | Metabolic rate constant for citrate [min$^{-1}$] (e.g., 0.0145 min$^{-1}$) |
| Rate_G_Ci | Citrate generation rate [mg/24 h] (e.g., 240 mg/24 h) |

INPUT VARIABLES FROM USER INTERFACE

| | |
|---|---|
| C_Ci_infusion | Concentration of citrate infusion [mmol/L] (e.g., 136 to 1600 mmol/L) |
| C_Ca_infusion | Concentration of calcium infusion [mmol/L] (e.g., 500 mmol/L) |

TABLE I-continued

| Explanation of variables used in program code excerpt | |
|---|---|
| Qb | Blood flow rate [L/min] (e.g., 0.2 to 0.5 L/min) |
| Hct_sys( ) | Systemic hematocrit at beginning of interval [vol-%/100] (e.g., 0.25 to 0.5) |
| Qd | Dialysate flow rate [L/min] (e.g., 0.4 to 0.8 L/min) |
| recirc_access | Access recirculation [%/100] (e.g., 0.05 to 0.2) |
| UFR( ) | Ultrafiltration rate [L/min] (e.g., 0.005 to 0.02 L/min) |
| Vurea | Urea distribution volume [L] (e.g., 25 to 70 L) |
| td | Dialysis treatment time [min] (e.g., 150 to 300 min) |
| tpost | Post-dialysis observation time to be modeled [min] (e.g., 60 to 300 min) |
| C_CaT_loc5 | Dialysate inlet total calcium concentration [mmol/L] (e.g., 0 to 2 mmol/L) |
| C_CiT_loc5 | Dialysate inlet total citrate concentration [mmol/L] (e.g., 0 to 2 mmol/L) |
| interval | Interval length (generic; used for all code and set to either interval_intra or interval_post, as applicable) [min] |
| interval_intra | Interval length for intradialytic iterations [min] (e.g., 0.017 to 1 min) |
| interval_post | Interval length for postdialytic iterations [min] (e.g. 1 min) |
| run_in | Interval length for run-in iteration [min] (e.g., $1.66 * 10^{-5}$ min) |
| wtgain | Current interdialytic weight gain [kg] (e.g., 0.5 to 5 kg) |
| KMP | Miscible calcium pool buffer coefficient [dimensionless] (e.g., 0.55 to 0.85) |
| VARIABLES FOR MODELING PROCESS | |
| Qb_sys( ) | "Systemic" blood flow rate [L/min] |
| Qb_loc1( ) | Blood flow rate at location 1 [L/min] |
| Qb_loc2( ) | Blood flow rate at location 2 [L/min] |
| Qb_loc3( ) | Blood flow rate at location 3 [L/min] |
| Qb_loc4( ) | Blood flow rate at location 4 [L/min] |
| R_p_wb_sys( ) | Ratio of plasma to whole blood systemically [dimensionless] |
| R_pw_wb_sys( ) | Ratio of plasma water to whole blood systemically [dimensionless] |
| R_p_wb_loc1( ) | Ratio of plasma to whole blood at location 1 [dimensionless] |
| R_pw_wb_loc1( ) | Ratio of plasma water to whole blood at location 1 [dimensionless] |
| R_p_wb_loc4( ) | Ratio of plasma to whole blood at location 4 [dimensionless] |
| R_pw_wb_loc4( ) | Ratio of plasma water to whole blood at location 4 [dimensionless] |
| C_CaT_sys_beg_wb( ) | Theoretical whole blood concentration of total calcium systemically at beginning of interval [mmol/L] |
| C_CiT_sys_beg_wb( ) | Theoretical whole blood concentration of total citrate systemically at beginning of interval [mmol/L] |
| C_prot_sys_beg_wb( ) | Theoretical whole blood concentration of total protein systemically at beginning of interval [mmol/L] |
| C_CaT_loc1_wb( ) | Theoretical whole blood concentration of total calcium at location 1 [mmol/L] |
| C_CiT_loc1_wb( ) | Theoretical whole blood concentration of total citrate at location 1 [mmol/L] |
| C_prot_loc1_wb( ) | Theoretical whole blood concentration of total protein at location 1 [mmol/L] |
| C_CaT_loc4_wb( ) | Theoretical whole blood concentration of total calcium at location 4 [mmol/L] |
| C_CiT_loc4_wb( ) | Theoretical whole blood concentration of total citrate at location 4 [mmol/L] |
| C_prot_loc4_wb( ) | Theoretical whole blood concentration of total protein at location 4 [mmol/L] |
| gs_iCa_default_sys | Goal seek iCa default for systemic iCa [mmol/L] (e.g., 1.5 mmol/L) |
| gs_iCa_default_loc2 | Goal seek iCa default for iCa at location 2 [mmol/L] (e.g., 0.05 or 1.5 mmol/L) |
| gs_iCa_default_loc3 | Goal seek iCa default for iCa at location 3 [mmol/L] (e.g., 0.4 or 1.5 mmol/L) |
| gs_iCa_default_loc4 | Goal seek iCa default for iCa at location 4 [mmol/L] (e.g., 1.5 mmol/L) |
| c | Iteration counter |
| req_iterations_HD | Required intradialytic iterations |
| req_iterations_post | Required postdialytic iterations |
| req_iterations | Required iterations for entire modeling process |
| reduction | Auxiliary variable used when iterating to determine the accurate citrate infusion rate required to reach the pre-filter iCa target [L/min] |
| dilution | Auxiliary variable used when iterating to determine the accurate citrate infusion rate required to reach the pre-filter iCa target [dimensionless] |
| actual_C_Cafree | Auxiliary variable used when iterating to determine the accurate citrate infusion rate required to reach the pre-filter iCa target. No location (_loc) is specified, so that this variable can be used for different locations (this is a temporary variable) [mmol/L] |
| actual_C_CiT | Auxiliary variable used when iterating to determine the accurate citrate infusion rate required to reach the pre-filter iCa target. No location (_loc) is specified, so that this variable can be used for different locations (this is a temporary variable) [mmol/L] |
| cf_Ca_mmol_to_mg | Conversion factor: calcium from mmol to mg [dimensionless] |
| time( ) | Elapsed time since start of hemodialysis treatment [min] |
| C_prot_sys_beg( ) | Total serum protein concentration systemically at beginning of interval [g/L] (e.g., 60 to 85 g/L) |

TABLE I-continued

| Explanation of variables used in program code excerpt | |
|---|---|
| C_prot_loc1( ) | Protein concentration at location 1 [g/L] |
| C_prot_loc4( ) | Protein concentration at location 4 [g/L] |
| C_bindingsites_sys_beg( ) | Concentration of calcium binding sites systemically at beginning of interval [mmol/L] |
| C_bindingsites_loc1( ) | Concentration of calcium binding sites at location 1 [mmol/L] |
| C_bindingsites_loc2( ) | Concentration of calcium binding sites at location 2 [mmol/L] |
| C_CaT_sys_beg( ) | Concentration of total calcium systemically at beginning of interval [mmol/L] (e.g., 2 to 2.6 mmol/L) |
| C_CaT_loc1( ) | Concentration of total calcium at location 1 [mmol/L] |
| C_CaT_loc2( ) | Concentration of total calcium at location 2 [mmol/L] |
| C_Cafree_loc2( ) | Concentration of free calcium at location 2 [mmol/L] |
| C_CiT_loc1( ) | Concentration of total citrate at location 1 [mmol/L] |
| C_CiT_loc2( ) | Concentration of total citrate at location 2 [mmol/L] |
| Qp_sys( ) | Plasma flow rate "systemically" (i.e., not accounting for access recirculation) [L/min] |
| Qp_loc1( ) | Plasma flow rate at location 1 [L/min] |
| Qp_loc2( ) | Plasma flow rate at location 2 [L/min] |
| Qp_loc3( ) | Plasma flow rate at location 3 [L/min] |
| Qp_loc4( ) | Plasma flow rate at location 4 [L/min] |
| Qpw_sys( ) | Plasma water flow rate "systemically" (i.e., not accounting for recirculation) [L/min] |
| Qpw_loc1( ) | Plasma water flow rate at location 1 [L/min] |
| Qpw_loc2( ) | Plasma water flow rate at location 2 [L/min] |
| Qpw_loc3( ) | Plasma water flow rate at location 3 [L/min] |
| Qpw_loc4( ) | Plasma water flow rate at location 4 [L/min] |
| Hct_loc1( ) | Hematocrit at location 1 [vol-%/100] |
| Hct_loc4( ) | Hematocrit at location 2 [vol-%/100] |
| C_CiT_sys_beg( ) | Concentration of total citrate systemically at beginning of interval [mmol/L] (e.g., 0.05 to 0.2 mmol/L) |
| Rate_Ci_infusion( ) | Citrate infusion rate [L/min] (e.g., 0 to 0.0083 L/min) |
| C_CaCi_loc2( ) | Concentration of calcium-citrate complexes at location 2 [mmol/L] |
| C_Cifree_loc5 | Dialysate inlet stream concentration of free citrate [mmol/L] |
| C_Cafree_loc5 | Dialysate inlet stream concentration of free calcium [mmol/L] |
| C_CaCi_loc5 | Dialysate inlet stream concentration of calcium-citrate complexes [mmol/L] |
| dC_CaCi( ) | Concentration gradient for calcium citrate complexes (dialysate-side concentration minus blood-side concentration) [mmol/L] |
| Qe_CaCi( ) | Effective solute diffusion volume flow rate for calcium-citrate complexes [L/min] |
| D_CaCi( ) | Dialysance of calcium-citrate complexes [L/min] |
| Jdiff_CaCi( ) | Diffusive flux of calcium-citrate complexes [mmol/min] |
| C_Cifree_loc2( ) | Concentration of free citrate at location 2 [mmol/L] |
| dC_Cifree( ) | Concentration gradient for free citrate (dialysate-side concentration minus blood-side concentration) [mmol/L] |
| Qe_Cifree | Effective solute diffusion volume flow rate for free citrate [L/min] |
| D_Cifree( ) | Dialysance of free citrate [L/min] |
| Jdiff_Cifree( ) | Diffusive flux of free citrate [mmol/min] |
| dC_Cafree( ) | Concentration gradient for free calcium (dialysate-side concentration minus blood-side concentration) [mmol/L] |
| Qe_Cafree( ) | Effective solute diffusion volume flow rate for free calcium [L/min] |
| D_Cafree( ) | Dialysance of free calcium [L/min] |
| Jdiff_Cafree( ) | Diffusive flux of free calcium [mmol/min] |
| Rate_CaCi_loc2( ) | Rate of calcium-citrate complexes entering dialyzer at blood inlet [mmol/min] |
| constr_Rate_CaCi_loc3( ) | Rate of calcium-citrate complexes leaving dialyzer at blood outlet, not considering convection [mmol/min] |
| constr_C_CaCi_loc3_unequ( ) | Hypothetical unequilibrated post-filter concentration of calcium-citrate complexes if ultrafiltration did not remove CaCi [mmol/L] |
| Rate_Cifree_loc2( ) | Rate of free citrate entering dialyzer at blood inlet [mmol/min] |
| constr_Rate_Cifree_loc3( ) | Rate of free citrate leaving dialyzer at blood outlet, not considering convection [mmol/min] |
| constr_C_Cifree_loc3_unequ( ) | Hypothetical unequilibrated post-filter concentration of free citrate if ultrafiltration did not remove free citrate [mmol/L] |
| Rate_Cafree_loc2( ) | Rate of free calcium entering dialyzer at blood inlet [mmol/min] |
| constr_Rate_Cafree_loc3( ) | Rate of free calcium leaving dialyzer at blood outlet, not considering convection [mmol/min] |
| constr_C_Cafree_loc3_unequ( ) | Hypothetical unequilibrated post-filter concentration of free calcium if ultrafiltration did not remove free calcium [mmol/L] |
| C_CaCi_forconvection( ) | Concentration of calcium-citrate complexes used for calculating convective flux [mmol/L] |
| C_Cifree_forconvection( ) | Concentration of free citrate used for calculating convective flux [mmol/L] |
| C_Cafree_forconvection( ) | Concentration of free calcium used for calculating convective flux [mmol/L] |
| Jconv_Cafree( ) | Convective flux of free calcium [mmol/min] |
| Jconv_CaCi( ) | Convective flux of calcium-citrate complexes [mmol/min] |
| Jconv_Cifree( ) | Convective flux of free citrate [mmol/min] |
| Jdiff_CaT( ) | Diffusive flux of calcium (of all forms) [mmol/min] |

TABLE I-continued

Explanation of variables used in program code excerpt

| Variable | Description |
|---|---|
| Jconv_CaT( ) | Convective flux of calcium (of all forms) [mmol/min] |
| Jtotal_CaT( ) | Total (diffusive and convective) flux of calcium (of all forms) [mmol/min] |
| Jdiff_CiT( ) | Diffusive flux of citrate (of all forms) [mmol/min] |
| Jconv_CiT( ) | Convective flux of citrate (of all forms) [mmol/min] |
| Jtotal_CiT( ) | Total (diffusive and convective) flux of citrate (of all forms) [mmol/min] |
| C_CaT_loc3( ) | Concentration of total calcium at location 3 [mmol/L] |
| C_CaT_loc4( ) | Concentration of total calcium at location 4 [mmol/L] |
| C_CiT_loc3( ) | Concentration of total citrate at location 3 [mmol/L] |
| C_CiT_loc4( ) | Concentration of total citrate at location 4 [mmol/L] |
| hc_factor( ) | Hemoconcentration factor (Qpwo/Qpwi) [dimensionless] |
| C_bindingsites_loc3( ) | Concentration of calcium binding sites at location 3 [mmol/L] |
| C_bindingsites_loc4( ) | Concentration of calcium binding sites at location 4 [mmol/L] |
| C_Cafree_loc3( ) | Concentration of free calcium at location 3 [mmol/L] |
| C_CaCi_loc3( ) | Concentration of calcium-citrate complexes at location 3 [mmol/L] |
| C_Cifree_loc3( ) | Concentration of free citrate at location 3 [mmol/L] |
| C_Cafree_loc4( ) | Concentration of free calcium at location 4 [mmol/L] |
| C_CaCi_loc4( ) | Concentration of calcium-citrate complexes at location 4 [mmol/L] |
| C_Cifree_loc4( ) | Concentration of free citrate at location 4 [mmol/L] |
| ECV_beg( ) | Estimated extracellular volume (ECV) at beginning of interval [L] |
| N_CiT_ECV_beg( ) | Amount of total citrate in ECV at beginning of interval [mmol] |
| N_CaT_ECV_beg( ) | Amount of total calcium in ECV at beginning of interval [mmol] |
| Rate_Ca_infusion( ) | Rate of calcium infusion [L/min] (e.g., 0.00067 L/min) |
| N_CiT_infused_interval( ) | Amount of citrate infused during interval [mmol] |
| N_CaT_infused_interval( ) | Amount of calcium substituted post-filter during interval [mmol] |
| dN_CiT_systemic_interval( ) | Net systemic change in total citrate during interval [mmol] |
| dN_CaT_systemic_interval( ) | Net systemic change in total calcium during interval [mmol] |
| N_CiT_ECV_end_noMETnoG( ) | Amount of total citrate in ECV at end of interval, not accounting for citrate generation or metabolism [mmol] |
| N_CaT_ECV_end_prebuffering( ) | Amount of total Ca in ECV at end of interval before calcium buffering [mmol] |
| UF_interval( ) | Ultrafiltration volume during interval [L] |
| Vol_Ci_infusion_interval( ) | Volume infused with citrate infusion during interval [L] |
| Vol_Ca_infusion_interval( ) | Volume infused with calcium substitution during interval [L] |
| ECV_end( ) | Estimated ECV at end of interval [L] |
| G_Ci_interval( ) | Generation of citrate during interval [mmol] |
| N_CiT_ECV_end_noMET( ) | Amount of total citrate in ECV at end of interval, accounting for citrate generation but not yet for metabolism [mmol] |
| C_CiT_ECV_end_noMET( ) | Concentration of total citrate in ECV at end of interval, accounting for citrate generation but not yet for metabolism [mmol/L] |
| average_C_CiT_sys_interval( ) | Average systemic citrate concentration between beginning and end of interval [mmol/L] |
| N_Ci_metabolized_interval( ) | Amount of citrate metabolized during interval [mmol] |
| N_CiT_ECV_end( ) | Amount of total citrate in ECV at end of interval, accounting for citrate generation, citrate metabolism, and dialyzer flux [mmol] |
| C_CiT_sys_end( ) | Systemic concentration of total citrate at end of interval [mmol/L] |
| MCa( ) | Mobilization/sequestration of Ca from/to miscible calcium pool [mmol] |
| C_CaT_sys_end( ) | Systemic concentration of total calcium at end of interval [mmol/L] |
| ECV_contractionfactor_interval( ) | ECV contraction factor for interval (ECV_beg/ECV_end) [dimensionless] |
| C_Cafree_sys_beg( ) | Systemic concentration of ionized calcium at beginning of interval [mmol/L] |

TABLE II

Sample code (VBA) for Simulation Mode 1
Note: This excerpt is intended to illustrate one possible implementation of the key elements of the model (simulation mode 1). Certain steps (e.g., re-dimensioning arrays, setting certain variables prior to first use, procedure for routing to specified simulation mode, calculation of cumulative parameters such as mass balances, reporting simulation results, etc.) are omitted.
Simulation modes 2 and 3 are also omitted, as they are adaptations of the presented code, and their implementation will be straightforward to a reader skilled in the art.

| | |
|---|---|
| Determining number of required iterations (1 is added to req_iterations_post so as to get 1 additional iteration; this will overshoot the intended post-HD observation time, but this iteration's values will be | req_iterations_HD = Round(td / interval_intra, 0)<br>req_iterations_post = Round(tpost / interval_post, 0) + 1<br>req_iterations = req_iterations_HD + req_iterations_post ' Note: Since we are working with option base 0, the run-in element is included in the array size if it is redimensioned to req_iterations |

TABLE II-continued

Sample code (VBA) for Simulation Mode 1
Note: This excerpt is intended to illustrate one possible implementation of the key elements of the model (simulation mode 1). Certain steps (e.g., re-dimensioning arrays, setting certain variables prior to first use, procedure for routing to specified simulation mode, calculation of cumulative parameters such as mass balances, reporting simulation results, etc.) are omitted.
Simulation modes 2 and 3 are also omitted, as they are adaptations of the presented code, and their implementation will be straightforward to a reader skilled in the art.

| | |
|---|---|
| required for printing/reporting.) | |
| Setting counter and starting time | run_in = 1 / 60000 ' 1 millisecond<br>c = 0<br>time(c) = 0 |
| Setting internal constants | cf_Ca_mmol_to_mg = 40.078 |
| Priming input variables from spreadsheet that are arrays (UFR, CaCl2 substitution and citrate infusion (if applicable) are not read here. They are read down in the iterations.) | Hct_sys(c) = rng_Hct_sys.Value / 100    ' [vol-%/100]<br>C_CiT_sys_beg(c) = rng_C_CiT_sys_beg.Value  ' [mmol/l]<br>C_CaT_sys_beg(c) = rng_C_CaT_sys_beg.Value  ' [mmol/l]<br>C_prot_sys_beg(c) = rng_C_prot_sys_beg.Value * 10  ' [g/l]<br>C_Cafree_loc2(c) = rng_C_Cafree_loc2.Value  ' [mmol/l] |
| Priming goal seek range | rng_gs_K_CaCi.Value = K_CaCi<br>rng_gs_K_CaP.Value = K_CaP<br>rng_gs_cubic.Value = "=D3 ^ 3 + D3 ^ 2 * (E3 + F3 + G3 + H3 − I3) + D3 * (E3 * F3 + F3 * G3 + E3 * H3 − E3 * I3 − F3 * I3) − E3 * F3 * I3" |
| Setting goal seek iCa defaults | gs_iCa_default_sys = 1.5<br><br>If sel_sim_mode = 3 Then<br>  gs_iCa_default_loc2 = 1.5<br>Else<br>  gs_iCa_default_loc2 = C_Cafree_loc2(c) + 0.05<br>End If<br>If sel_sim_mode = 3 Then<br>  gs_iCa_default_loc3 = 1.5<br>Else<br>  gs_iCa_default_loc3 = C_Cafree_loc2(c) + 0.4<br>End If<br>gs_iCa_default_loc4 = 1.5 |
| FIRST ITERATION | |
| Set Qb and Qp at sys and loc1 | Qb_sys(c) = Qb<br>Qb_loc1(c) = Qb<br>Qp_sys(c) = (1 − Hct_sys(c)) * Qb_sys(c)<br>Qp_loc1(c) = Qp_sys(c) |
| (run-in iteration; no recirculation considered) | |
| Set interval length | interval = run_in |
| Systemic conc. of binding sites at beginning of interval | C_bindingsites_sys_beg(c) = (12 * C_prot_sys_beg(c) / 69000) * 1000 |
| Conc. of binding sites at loc1 (not accounting for access recirculation, since this is run-in iteration) | C_bindingsites_loc1(c) = C_bindingsites_sys_beg(c) |
| Total calcium and citrate concentrations at loc1 (run-in iteration; not accounting for access recirculation) | C_CaT_loc1(c) = C_CaT_sys_beg(c)<br>C_CiT_loc1(c) = C_CiT_sys_beg(c) |
| Required citrate conc. in plasma water inlet stream to reach pre-filter iCa target (ignoring the dilution caused by the citrate infusion) | C_CiT_loc2(c) = (−C_Cafree_loc2(c) ^ 3 − C_Cafree_loc2(c) ^ 2 * K_CaCi − C_Cafree_loc2(c) ^ 2 * K_CaP − C_Cafree_loc2(c) ^ 2 * C_bindingsites_loc1(c) + C_Cafree_loc2(c) ^ 2 * C_CaT_loc1(c) − C_Cafree_loc2(c) * K_CaCi * K_CaP − C_Cafree_loc2(c) * K_CaCi * C_bindingsites_loc1(c) + C_Cafree_loc2(c) * K_CaCi * C_CaT_loc1(c) + C_Cafree_loc2(c) * K_CaP * C_CaT_loc1(c) + K_CaCi * K_CaP * C_CaT_loc1(c)) / (C_Cafree_loc2(c) ^ 2 + C_Cafree_loc2(c) * K_CaP) |
| Serum protein concentration at loc1 (run-in iteration; not accounting for access recirculation) | C_prot_loc1(c) = C_prot_sys_beg(c) ' run-in iteration; recirculation not considered |
| Plasma water flow rate at loc1 | Qpw_loc1(c) = Qp_loc1(c) * (0.989 − 0.0074 * (C_prot_loc1(c) / 10)) |
| Required rate of citrate infusion to reach pre-filter iCa target | Rate_Ci_infusion(c) = (Qpw_loc1(c) * (C_CiT_loc1(c) − C_CiT_loc2(c))) / (C_CiT_loc2(c) − C_Ci_infusion) |
| Resulting pwi flow | Qpw_loc2(c) = Qpw_loc1(c) + Rate_Ci_infusion(c) |
| Iterating to find true rate of citrate infusion required | If sel_skip_Ci_infusion_iteration = False Then |

TABLE II-continued

Sample code (VBA) for Simulation Mode 1
Note: This excerpt is intended to illustrate one possible implementation of the key
elements of the model (simulation mode 1). Certain steps (e.g., re-dimensioning arrays,
setting certain variables prior to first use, procedure for routing to specified simulation
mode, calculation of cumulative parameters such as mass balances, reporting simulation
results, etc.) are omitted.
Simulation modes 2 and 3 are also omitted, as they are adaptations of the presented code,
and their implementation will be straightforward to a reader skilled in the art.

| | |
|---|---|
| (since the above does not account for dilution caused by the citrate infusion itself) | reduction = 0<br>dilution = (Qpw__loc2(c) − reduction) / Qpw__loc1(c)<br>C__CaT__loc2(c) = C__CaT__loc1(c) / dilution<br>C__bindingsites__loc2(c) = C__bindingsites__loc1(c) / dilution |
| (Goal seek for pre-filter ionized calcium) | rng__gs__iCa.Value = gs__iCa__default__loc2<br>rng__gs__C__CiT.Value = C__CiT__loc2(c)<br>rng__gs__C__bindingsites.Value = C__bindingsites__loc2(c)<br>rng__gs__C__CaT.Value = C__CaT__loc2(c)<br>rng__gs__cubic.GoalSeek Goal:=0, ChangingCell:=rng__gs__iCa<br>actual__C__Cafree = rng__gs__iCa.Value<br>If actual__C__Cafree > C__Cafree__loc2(c) Then<br>  MsgBox ("Actual pre-filter iCa was already > target to begin with!")<br>  Exit Sub<br>End If<br>If sel__use__iCa__tolerance = True Then<br>  If actual__C__Cafree > C__Cafree__loc2(c) − tolerance__Cafree__loc2 Then<br>    GoTo leave__match__sim1__iter1<br>End If<br>If Rate__Ci__infusion(c) − (reduction + reduction__step) <= 0 Then GoTo<br>  leave__match__sim1__iter1<br>Do<br>  reduction = reduction + reduction__step<br>  dilution = (Qpw__loc2(c) − reduction) / Qpw__loc1(c)<br>  C__CaT__loc2(c) = C__CaT__loc1(c) / dilution<br>  C__bindingsites__loc2(c) = C__bindingsites__loc1(c) / dilution<br>  actual__C__CiT = (C__Ci__infusion * (Rate__Ci__infusion(c) − reduction) +<br>    C__CiT__loc1(c) * Qpw__loc1(c)) / (Rate__Ci__infusion(c) − reduction +<br>    Qpw__loc1(c)) |
| (Goal seek for pre-filter ionized calcium) | rng__gs__iCa.Value = gs__iCa__default__loc2<br>rng__gs__C__CiT.Value = actual__C__CiT<br>rng__gs__C__bindingsites.Value = C__bindingsites__loc2(c)<br>rng__gs__C__CaT.Value = C__CaT__loc2(c)<br>rng__gs__cubic.GoalSeek Goal:=0, ChangingCell:=rng__gs__iCa<br>actual__C__Cafree = rng__gs__iCa.Value<br>If actual__C__Cafree > C__Cafree__loc2(c) Then GoTo<br>  leave__overshot__sim1__iter1<br>If sel__use__iCa__tolerance = True Then<br>  If actual__C__Cafree > C__Cafree__loc2(c) − tolerance__Cafree__loc2 Then<br>    GoTo leave__match__sim1__iter1<br>End If<br>If Rate__Ci__infusion(c) − (reduction + reduction__step) <= 0 Then GoTo<br>  leave__match__sim1__iter1<br>Loop<br>leave__overshot__sim1__iter1:<br>  reduction = reduction − reduction__step<br>  Rate__Ci__infusion(c) = Rate__Ci__infusion(c) − reduction<br>  Qpw__loc2(c) = Qpw__loc1(c) + Rate__Ci__infusion(c)<br>  dilution = (Qpw__loc2(c) − reduction) / Qpw__loc1(c)<br>  C__CaT__loc2(c) = C__CaT__loc1(c) / dilution<br>  C__bindingsites__loc2(c) = C__bindingsites__loc1(c) / dilution<br>  C__CiT__loc2(c) = (C__Ci__infusion * (Rate__Ci__infusion(c) − reduction) +<br>    C__CiT__loc1(c) * Qpw__loc1(c)) / (Rate__Ci__infusion(c) − reduction +<br>    Qpw__loc1(c))<br>leave__match__sim1__iter1:<br>  Rate__Ci__infusion(c) = Rate__Ci__infusion(c) − reduction<br>  Qpw__loc2(c) = Qpw__loc1(c) + Rate__Ci__infusion(c)<br>  C__CiT__loc2(c) = actual__C__CiT<br>End If |
| Concentration of calcium-citrate complexes pre-filter | C__CaCi__loc2(c) = ((C__Cafree__loc2(c) * C__CiT__loc2(c)) / (K__CaCi + C__Cafree__loc2(c))) |
| Determine dialysate composition (free citrate, free calcium, calcium-citrate complexes) | C__Cifree__loc5 = −0.5 * (C__CaT__loc5 − C__CiT__loc5 + K__CaCi) + Sqr((0.5 * (C__CaT__loc5 − C__CiT__loc5 + K__CaCi)) ^ 2 + (K__CaCi * C__CiT__loc5))<br>If C__CiT__loc5 = 0 Then<br>  C__Cafree__loc5 = C__CaT__loc5<br>Else<br>  C__Cafree__loc5 = (K__CaCi * (C__CiT__loc5 − C__Cifree__loc5)) / C__Cifree__loc5<br>End If<br>C__CaCi__loc5 = (C__Cafree__loc5 * C__Cifree__loc5) / K__CaCi |

TABLE II-continued

Sample code (VBA) for Simulation Mode 1
Note: This excerpt is intended to illustrate one possible implementation of the key elements of the model (simulation mode 1). Certain steps (e.g., re-dimensioning arrays, setting certain variables prior to first use, procedure for routing to specified simulation mode, calculation of cumulative parameters such as mass balances, reporting simulation results, etc.) are omitted.
Simulation modes 2 and 3 are also omitted, as they are adaptations of the presented code, and their implementation will be straightforward to a reader skilled in the art.

DIFFUSIVE FLUXES

| | |
|---|---|
| Calculate diffusive flux of calcium-citrate complexes across the dialyzer membrane | dC_CaCi(c) = C_CaCi_loc5 − C_CaCi_loc2(c)<br>Qe_CaCi(c) = Qpw_loc2(c)<br>D_CaCi(c) = ((Exp(((1 / Qe_CaCi(c)) − (1 / Qd)) * KoA_CaCi) − 1) / (Exp(((1 / Qe_CaCi(c)) − (1 / Qd)) * KoA_CaCi − (Qe_CaCi(c) / Qd))) * Qe_CaCi(c)<br>Jdiff_CaCi(c) = D_CaCi(c) * dC_CaCi(c)<br>C_Cifree_loc2(c) = C_CiT_loc2(c) − C_CaCi_loc2(c)<br>dC_Cifree(c) = C_Cifree_loc5 − C_Cifree_loc2(c) |
| Calculate diffusive flux of free citrate across the dialyzer membrane | Qe_Cifree(c) = Qpw_loc2(c)<br>D_Cifree(c) = ((Exp(((1 / Qe_Cifree(c)) − (1 / Qd)) * KoA_Cifree) − 1) / (Exp(((1 / Qe_Cifree(c)) − (1 / Qd)) * KoA_Cifree − (Qe_Cifree(c) / Qd))) * Qe_Cifree(c)<br>Jdiff_Cifree(c) = D_Cifree(c) * dC_Cifree(c) |
| Calculate diffusive flux of free calcium across the dialyzer membrane | dC_Cafree(c) = C_Cafree_loc5 − C_Cafree_loc2(c)<br>Qe_Cafree(c) = Qpw_loc2(c)<br>D_Cafree(c) = ((Exp(((1 / Qe_Cafree(c)) − (1 / Qd)) * KoA_Cafree) − 1) / (Exp(((1 / Qe_Cafree(c)) − (1 / Qd)) * KoA_Cafree − (Qe_Cafree(c) / Qd))) * Qe_Cafree(c)<br>Jdiff_Cafree(c) = D_Cafree(c) * dC_Cafree(c) |
| Rates of calcium-citrate complexes, free citrate, and free calcium entering the dialyzer | Rate_CaCi_loc2(c) = C_CaCi_loc2(c) * Qpw_loc2(c)<br>Rate_Cifree_loc2(c) = C_Cifree_loc2(c) * Qpw_loc2(c)<br>Rate_Cafree_loc2(c) = C_Cafree_loc2(c) * Qpw_loc2(c) |
| Read current ultrafiltration rate | UFR(c) = Application.WorksheetFunction.VLookup(time(c), rng_UFR, 2, True) / (60000) |
| Concentration constructs (for solutes leaving blood outlet) for calculating convective flux | constr_Rate_CaCi_loc3(c) = Rate_CaCi_loc2(c) + Jdiff_CaCi(c)<br>constr_C_CaCi_loc3_unequ(c) = constr_Rate_CaCi_loc3(c) / (Qpw_loc2(c) − UFR(c))<br>constr_Rate_Cifree_loc3(c) = Rate_Cifree_loc2(c) + Jdiff_Cifree(c)<br>constr_C_Cifree_loc3_unequ(c) = constr_Rate_Cifree_loc3(c) / (Qpw_loc2(c) − UFR(c))<br>constr_Rate_Cafree_loc3(c) = Rate_Cafree_loc2(c) + Jdiff_Cafree(c)<br>constr_C_Cafree_loc3_unequ(c) = constr_Rate_Cafree_loc3(c) / (Qpw_loc2(c) − UFR(c)) |
| Concentrations used for calculating convective losses | C_CaCi_forconvection(c) = (C_CaCi_loc2(c) + 2 * constr_C_CaCi_loc3_unequ(c)) / 3<br>C_Cifree_forconvection(c) = (C_Cifree_loc2(c) + 2 * constr_C_Cifree_loc3_unequ(c)) / 3<br>C_Cafree_forconvection(c) = (C_Cafree_loc2(c) + 2 * constr_C_Cafree_loc3_unequ(c)) / 3 |
| CONVECTIVE FLUXES of free calcium, calcium-citrate complexes, and free citrate | Jconv_Cafree(c) = −C_Cafree_forconvection(c) * UFR(c)<br>Jconv_CaCi(c) = −C_CaCi_forconvection(c) * UFR(c)<br>Jconv_Cifree(c) = −C_Cifree_forconvection(c) * UFR(c) |

TOTAL FLUXES

| | |
|---|---|
| Total calcium flux | Jdiff_CaT(c) = Jdiff_CaCi(c) + Jdiff_Cafree(c)<br>Jconv_CaT(c) = Jconv_Cafree(c) + Jconv_CaCi(c)<br>Jtotal_CaT(c) = Jdiff_CaT(c) + Jconv_CaT(c) |
| Total citrate flux | Jdiff_CiT(c) = Jdiff_CaCi(c) + Jdiff_Cifree(c)<br>Jconv_CiT(c) = Jconv_CaCi(c) + Jconv_Cifree(c)<br>Jtotal_CiT(c) = Jdiff_CiT(c) + Jconv_CiT(c) |
| Post-filter concentrations of total calcium and total citrate | Qpw_loc3(c) = Qpw_loc2(c) − UFR(c)<br>C_CaT_loc3(c) = ((C_CaT_loc2(c) * Qpw_loc2(c)) + Jtotal_CaT(c)) / (Qpw_loc3(c))<br>C_CiT_loc3(c) = ((C_CiT_loc2(c) * Qpw_loc2(c)) + Jtotal_CiT(c)) / (Qpw_loc3(c)) |
| Equilibrated post-filter concentrations of free calcium, free citrate, and calcium-citrate complexes | hc_factor(c) = Qpw_loc3(c) / Qpw_loc2(c)<br>C_bindingsites_loc3(c) = C_bindingsites_loc2(c) / hc_factor(c) |
| Goal seek for post-filter ionized calcium (loc3) | rng_gs_iCa.Value = gs_iCa_default_loc3<br>rng_gs_C_CiT.Value = C_CiT_loc3(c)<br>rng_gs_C_bindingsites.Value = C_bindingsites_loc3(c)<br>rng_gs_C_CaT.Value = C_CaT_loc3(c)<br>rng_gs_cubic.GoalSeek Goal:=0, ChangingCell:=rng_gs_iCa<br>C_Cafree_loc3(c) = rng_gs_iCa.Value<br>C_CaCi_loc3(c) = ((C_Cafree_loc3(c) * C_CiT_loc3(c)) / (K_CaCi + C_Cafree_loc3(c)))<br>C_Cifree_loc3(c) = C_CiT_loc3(c) − C_CaCi_loc3(c) |

TABLE II-continued

Sample code (VBA) for Simulation Mode 1
Note: This excerpt is intended to illustrate one possible implementation of the key elements of the model (simulation mode 1). Certain steps (e.g., re-dimensioning arrays, setting certain variables prior to first use, procedure for routing to specified simulation mode, calculation of cumulative parameters such as mass balances, reporting simulation results, etc.) are omitted.
Simulation modes 2 and 3 are also omitted, as they are adaptations of the presented code, and their implementation will be straightforward to a reader skilled in the art.

| | |
|---|---|
| Read current Ca infusion rate [l/min] | Rate_Ca_infusion(c) = Application.WorksheetFunction.VLookup(time(c), rng_Ca_infusion, 2, True) / (60000) |
| Blood, plasma, and plasma water flow rates at loc4 | Qpw_loc4(c) = Qpw_loc3(c) + Rate_Ca_infusion(c)<br>Qb_loc4(c) = Qb_loc1(c) + Rate_Ci_infusion(c) − UFR(c) + Rate_Ca_infusion(c) |
| Ratio of plasma water to whole blood at loc4 | R_pw_wb_loc4(c) = Qpw_loc4(c) / Qb_loc4(c) |
| Post-Ca-infusion concentrations of total calcium and total citrate (loc4) | C_CaT_loc4(c) = (C_CaT_loc3(c) * Qpw_loc3(c) + C_Ca_infusion * Rate_Ca_infusion(c)) / Qpw_loc4(c)<br>C_CiT_loc4(c) = (C_CiT_loc3(c) * Qpw_loc3(c)) / Qpw_loc4(c) |
| Plasma flow rate at loc4 | Qp_loc4(c) = Qp_loc1(c) + Rate_Ci_infusion(c) − UFR(c) + Rate_Ca_infusion(c) |
| Serum protein concentration at loc4 | C_prot_loc4(c) = C_prot_loc1(c) / (Qp_loc4(c) / Qp_loc1(c)) |
| Ratio of plasma to whole blood at loc4 | R_p_wb_loc4(c) = Qp_loc4(c) / Qb_loc4(c) |
| Hematocrit at loc4 | Hct_loc4(c) = (Qb_loc4(c) − Qp_loc4(c)) / Qb_loc4(c) |
| Theoretical whole blood concentrations of relevant solutes (used for recirculation) | C_CaT_loc4_wb(c) = C_CaT_loc4(c) * R_pw_wb_loc4(c)<br>C_CiT_loc4_wb(c) = C_CiT_loc4(c) * R_pw_wb_loc4(c)<br>C_prot_loc4_wb(c) = C_prot_loc4(c) * R_p_wb_loc4(c) |
| Equilibrated post-Ca-infusion concentrations of free calcium, free citrate, and calcium-citrate complexes | hc_factor(c) = Qpw_loc4(c) / Qpw_loc3(c)<br>C_bindingsites_loc4(c) = C_bindingsites_loc3(c) / hc_factor(c)<br>' Goal seek for post-Ca-infusion ionized Ca (loc4)<br>   rng_gs_iCa.Value = gs_iCa_default_loc4<br>   rng_gs_C_CiT.Value = C_CiT_loc4(c)<br>   rng_gs_C_bindingsites.Value = C_bindingsites_loc4(c)<br>   rng_gs_C_CaT.Value = C_CaT_loc4(c)<br>   rng_gs_cubic.GoalSeek Goal:=0, ChangingCell:=rng_gs_iCa<br>C_Cafree_loc4(c) = rng_gs_iCa.Value<br>C_CaCi_loc4(c) = ((C_Cafree_loc4(c) * C_CiT_loc4(c)) / (K_CaCi + C_Cafree_loc4(c)))<br>C_Cifree_loc4(c) = C_CiT_loc4(c) − C_CaCi_loc4(c) |
| ECV at beginning of interval | ECV_beg(c) = (Vurea / 3) + wtgain |
| Amounts of citrate and calcium in ECV at beginning of interval | N_CiT_ECV_beg(c) = C_CiT_sys_beg(c) * ECV_beg(c)<br>N_CaT_ECV_beg(c) = C_CaT_sys_beg(c) * ECV_beg(c) |
| Amounts of citrate and calcium infused during interval | N_CiT_infused_interval(c) = Rate_Ci_infusion(c) * C_Ci_infusion * interval<br>N_CaT_infused_interval(c) = Rate_Ca_infusion(c) * C_Ca_infusion * interval |
| Net systemic changes in total citrate and total calcium during interval | dN_CiT_systemic_interval(c) = (Jtotal_CiT(c) * interval) + N_CiT_infused_interval(c)<br>dN_CaT_systemic_interval(c) = (Jtotal_CaT(c) * interval) + N_CaT_infused_interval(c) |
| Amount of citrate in ECV at end of interval, not considering citrate generation or metabolism | N_CiT_ECV_end_noMETnoG(c) = N_CiT_ECV_beg(c) + dN_CiT_systemic_interval(c) |
| Amount of total calcium in ECV at end of interval, not considering buffering. Note that this is the unbuffered amount for this particular interval, but it is the buffered amount that is carried forward to the beginning of the next interval, which will be different if KMP is not equal to 0. | N_CaT_ECV_end_prebuffering(c) = N_CaT_ECV_beg(c) + dN_CaT_systemic_interval(c) |
| | UF_interval(c) = UFR(c) * interval<br>Vol_Ci_infusion_interval(c) = Rate_Ci_infusion(c) * interval<br>Vol_Ca_infusion_interval(c) = Rate_Ca_infusion(c) * interval |
| ECV at end of interval | ECV_end(c) = ECV_beg(c) − UF_interval(c) + Vol_Ci_infusion_interval(c) + Vol_Ca_infusion_interval(c) |
| Citrate generation rate during interval | G_Ci_interval(c) = ((Rate_G_Ci * interval) / (24 * 60)) / (192.12352) |

TABLE II-continued

Sample code (VBA) for Simulation Mode 1
Note: This excerpt is intended to illustrate one possible implementation of the key elements of the model (simulation mode 1). Certain steps (e.g., re-dimensioning arrays, setting certain variables prior to first use, procedure for routing to specified simulation mode, calculation of cumulative parameters such as mass balances, reporting simulation results, etc.) are omitted.
Simulation modes 2 and 3 are also omitted, as they are adaptations of the presented code, and their implementation will be straightforward to a reader skilled in the art.

| | |
|---|---|
| Amount of citrate in ECV at end of interval, considering citrate generation but not metabolism | N_CiT_ECV_end_noMET(c) = N_CiT_ECV_end_noMETnoG(c) + G_Ci_interval(c) |
| Citrate concentration in ECV at end of interval, considering citrate generation but not metabolism | C_CiT_ECV_end_noMET(c) = N_CiT_ECV_end_noMET(c) / ECV_end(c) |
| | average_C_CiT_sys_interval(c) = WorksheetFunction.Average(C_CiT_ECV_end_noMET(c), C_CiT_sys_beg(c)) |
| Amount of citrate metabolized during interval | N_Ci_metabolized_interval(c) = N_CiT_ECV_end_noMET(c) − (average_C_CiT_sys_interval(c) * Exp(−k_Ci * interval) * WorksheetFunction.Average(ECV_end(c), ECV_beg(c))) |
| Amount of citrate in ECV at end of interval, considering generation and metabolism | N_CiT_ECV_end(c) = N_CiT_ECV_end_noMET(c) − N_Ci_metabolized_interval(c) |
| Total systemic citrate conc. at end of interval | C_CiT_sys_end(c) = N_CiT_ECV_end(c) / ECV_end(c) |
| Mobilization/sequestration of calcium during interval | MCa(c) = −((Jdiff_CaT(c) * interval) + N_CaT_infused_interval(c)) * KMP |
| Total systemic calcium concentration at end of interval | C_CaT_sys_end(c) = (N_CaT_ECV_end_prebuffering(c) + MCa(c)) / ECV_end(c) |
| ECV contraction factor for interval | ECV_contractionfactor_interval(c) = ECV_beg(c) / ECV_end(c) |
| Goal seek for systemic ionized calcium at beginning of interval | rng_gs_iCa.Value = gs_iCa_default_sys<br>rng_gs_C_CiT.Value = C_CiT_sys_beg(c)<br>rng_gs_C_bindingsites.Value = C_bindingsites_sys_beg(c)<br>rng_gs_C_CaT.Value = C_CaT_sys_beg(c)<br>rng_gs_cubic.GoalSeek Goal:=0, ChangingCell:=rng_gs_iCa<br>C_Cafree_sys_beg(c) = rng_gs_iCa.Value |
| REMAINING INTRADIALYTIC ITERATIONS | |
| Set the interval length back from the run_in interval length to the user-defined interval length for the intradialytic iterations | interval = interval_intra |
| Set time(0) to 0 − interval so that the following iterations will start from time(1) = 0 minutes. (This is done here instead of right from the start because 0 − interval is negative, which would cause the VLookup function in the first iteration to fail.) | time(c) = 0 − interval |
| | Do<br>  c = c + 1<br>  time(c) = time(c − 1) + interval |
| Systemic concentration of total protein | C_prot_sys_beg(c) = C_prot_sys_beg(c − 1) * ECV_contractionfactor_interval(c − 1) |
| Systemic concentration of binding sites at beginning of interval | C_bindingsites_sys_beg(c) = (12 * C_prot_sys_beg(c) / 69000) * 1000 |
| Total systemic calcium and citrate concentrations at beginning of interval | C_CaT_sys_beg(c) = C_CaT_sys_end(c − 1)<br>C_CiT_sys_beg(c) = C_CiT_sys_end(c − 1) |
| Systemic hematocrit at beginning of interval | Hct_sys(c) = Hct_sys(c − 1) / (Hct_sys(c − 1) + ((1 − Hct_sys(c − 1)) / ECV_contractionfactor_interval(c − 1))) |
| "Systemic" plasma and plasma water flow rates | Qp_sys(c) = Qb * (1 − Hct_sys(c))<br>Qpw_sys(c) = Qp_sys(c) * (0.989 − 0.0074 * (C_prot_sys_beg(c) / 10)) |
| Systemic ratios of plasma to whole blood and plasma water to whole blood | R_p_wb_sys(c) = Qp_sys(c) / Qb<br>R_pw_wb_sys(c) = Qpw_sys(c) / Qb |

TABLE II-continued

Sample code (VBA) for Simulation Mode 1
Note: This excerpt is intended to illustrate one possible implementation of the key elements of the model (simulation mode 1). Certain steps (e.g., re-dimensioning arrays, setting certain variables prior to first use, procedure for routing to specified simulation mode, calculation of cumulative parameters such as mass balances, reporting simulation results, etc.) are omitted.
Simulation modes 2 and 3 are also omitted, as they are adaptations of the presented code, and their implementation will be straightforward to a reader skilled in the art.

| | |
|---|---|
| Theoretical systemic whole blood concentrations of relevant solutes (for recirculation) | C_prot_sys_beg_wb(c) = C_prot_sys_beg(c) * R_p_wb_sys(c)<br>C_CaT_sys_beg_wb(c) = C_CaT_sys_beg(c) * R_pw_wb_sys(c)<br>C_CiT_sys_beg_wb(c) = C_CiT_sys_beg(c) * R_pw_wb_sys(c) |
| Hematocrit at loc1 | Hct_loc1(c) = recirc_access * Hct_loc4(c − 1) + (1 − recirc_access) * Hct_sys(c) |
| Blood and plasma flow rates at loc1, and the ratio of plasma to whole blood at loc1 | Qb_loc1(c) = Qb<br>Qp_loc1(c) = Qb_loc1(c) * (1 − Hct_loc1(c))<br>R_p_wb_loc1(c) = Qp_loc1(c) / Qb_loc1(c) |
| Protein concentration at loc1:<br>1) Theoretical whole blood concentration<br>2) Plasma concentration | C_prot_loc1_wb(c) = recirc_access * (C_prot_loc4_wb(c − 1)) + (1 − recirc_access) * C_prot_sys_beg_wb(c)<br>C_prot_loc1(c) = C_prot_loc1_wb(c) / R_p_wb_loc1(c) |
| Plasma water flow rate at loc1 | Qpw_loc1(c) = Qp_loc1(c) * (0.989 − 0.0074 * (C_prot_loc1(c) / 10)) |
| Ratio of plasma water to whole blood at loc1 | R_pw_wb_loc1(c) = Qpw_loc1(c) / Qb_loc1(c) |
| Total calcium and citrate concentrations at loc1 (accounting for recirculation)<br>1) as theoretical whole blood concentrations | C_CaT_loc1_wb(c) = recirc_access * C_CaT_loc4_wb(c − 1) + (1 − recirc_access) * C_CaT_sys_beg_wb(c)<br>C_CiT_loc1_wb(c) = recirc_access * C_CiT_loc4_wb(c − 1) + (1 − recirc_access) * C_CiT_sys_beg_wb(c) |
| 2) reverting to plasma water concentrations | C_CaT_loc1(c) = C_CaT_loc1_wb(c) / R_pw_wb_loc1(c)<br>C_CiT_loc1(c) = C_CiT_loc1_wb(c) / R_pw_wb_loc1(c) |
| Concentration of calcium binding sites at loc1 | C_bindingsites_loc1(c) = (12 * C_prot_loc1(c) / 69000) * 1000 |
| Plasma water and citrate infusion flow rates and the resulting pre-filter total citrate concentration | Rate_Ci_infusion(c) = Rate_Ci_infusion(c − 1)<br>Qpw_loc2(c) = Qpw_loc1(c) + Rate_Ci_infusion(c)<br>C_CiT_loc2(c) = (C_Ci_infusion * Rate_Ci_infusion(c) + C_CiT_loc1(c) * Qpw_loc1(c)) / Qpw_loc2(c) |
| Determining the resulting pre-filter ionized calcium concentration | dilution = Qpw_loc2(c) / Qpw_loc1(c)<br>C_CaT_loc2(c) = C_CaT_loc1(c) / dilution<br>C_bindingsites_loc2(c) = C_bindingsites_loc1(c) / dilution<br>rng_gs_iCa.Value = gs_iCa_default_loc2<br>rng_gs_C_CiT.Value = C_CiT_loc2(c)<br>rng_gs_C_bindingsites.Value = C_bindingsites_loc2(c)<br>rng_gs_C_CaT.Value = C_CaT_loc2(c)<br>rng_gs_cubic.GoalSeek Goal:=0, ChangingCell:=rng_gs_iCa<br>C_Cafree_loc2(c) = rng_gs_iCa.Value |
| Concentration of calcium-citrate complexes pre-filter | C_CaCi_loc2(c) = ((C_Cafree_loc2(c) * C_CiT_loc2(c)) / (K_CaCi + C_Cafree_loc2(c))) |
| DIFFUSIVE FLUXES | |
| Diffusive flux of calcium-citrate complexes | dC_CaCi(c) = C_CaCi_loc5 − C_CaCi_loc2(c)<br>Qe_CaCi(c) = Qpw_loc2(c)<br>D_CaCi(c) = ((Exp(((1 / Qe_CaCi(c)) − (1 / Qd)) * KoA_CaCi) − 1) / (Exp(((1 / Qe_CaCi(c)) − (1 / Qd)) * KoA_CaCi − (Qe_CaCi(c) / Qd))) * Qe_CaCi(c)<br>Jdiff_CaCi(c) = D_CaCi(c) * dC_CaCi(c) |
| Diffusive flux of free citrate | C_Cifree_loc2(c) = C_CiT_loc2(c) − C_CaCi_loc2(c)<br>dC_Cifree(c) = C_Cifree_loc5 − C_Cifree_loc2(c)<br>Qe_Cifree(c) = Qpw_loc2(c)<br>D_Cifree(c) = ((Exp(((1 / Qe_Cifree(c)) − (1 / Qd)) * KoA_Cifree) − 1) / (Exp(((1 / Qe_Cifree(c)) − (1 / Qd)) * KoA_Cifree − (Qe_Cifree(c) / Qd))) * Qe_Cifree(c)<br>Jdiff_Cifree(c) = D_Cifree(c) * dC_Cifree(c) |
| Diffusive flux of free calcium | dC_Cafree(c) = C_Cafree_loc5 − C_Cafree_loc2(c)<br>Qe_Cafree(c) = Qpw_loc2(c)<br>D_Cafree(c) = ((Exp(((1 / Qe_Cafree(c)) − (1 / Qd)) * KoA_Cafree) − 1) / (Exp(((1 / Qe_Cafree(c)) − (1 / Qd)) * KoA_Cafree − (Qe_Cafree(c) / Qd))) * Qe_Cafree(c)<br>Jdiff_Cafree(c) = D_Cafree(c) * dC_Cafree(c) |
| Rates of calcium-citrate complexes, free citrate, and free calcium entering the dialyzer | Rate_CaCi_loc2(c) = C_CaCi_loc2(c) * Qpw_loc2(c)<br>Rate_Cifree_loc2(c) = C_Cifree_loc2(c) * Qpw_loc2(c)<br>Rate_Cafree_loc2(c) = C_Cafree_loc2(c) * Qpw_loc2(c) |

TABLE II-continued

Sample code (VBA) for Simulation Mode 1
Note: This excerpt is intended to illustrate one possible implementation of the key elements of the model (simulation mode 1). Certain steps (e.g., re-dimensioning arrays, setting certain variables prior to first use, procedure for routing to specified simulation mode, calculation of cumulative parameters such as mass balances, reporting simulation results, etc.) are omitted.
Simulation modes 2 and 3 are also omitted, as they are adaptations of the presented code, and their implementation will be straightforward to a reader skilled in the art.

| | |
|---|---|
| Read current ultrafiltration rate | UFR(c) = Application.WorksheetFunction.VLookup(time(c), rng__UFR, 2, True) / (60000) |
| Concentration constructs (for solutes leaving blood outlet) for calculating convective flux | constr__Rate__CaCi__loc3(c) = Rate__CaCi__loc2(c) + Jdiff__CaCi(c)<br>constr__C__CaCi__loc3__unequ(c) = constr__Rate__CaCi__loc3(c) / (Qpw__loc2(c) − UFR(c))<br>constr__Rate__Cifree__loc3(c) = Rate__Cifree__loc2(c) + Jdiff__Cifree(c)<br>constr__C__Cifree__loc3__unequ(c) = constr__Rate__Cifree__loc3(c) / (Qpw__loc2(c) − UFR(c))<br>constr__Rate__Cafree__loc3(c) = Rate__Cafree__loc2(c) + Jdiff__Cafree(c)<br>constr__C__Cafree__loc3__unequ(c) = constr__Rate__Cafree__loc3(c) / (Qpw__loc2(c) − UFR(c)) |
| Concentrations used for calculating convective losses | C__CaCi__forconvection(c) = (C__CaCi__loc2(c) + 2 * constr__C__CaCi__loc3__unequ(c)) / 3<br>C__Cifree__forconvection(c) = (C__Cifree__loc2(c) + 2 * constr__C__Cifree__loc3__unequ(c)) / 3<br>C__Cafree__forconvection(c) = (C__Cafree__loc2(c) + 2 * constr__C__Cafree__loc3__unequ(c)) / 3 |
| CONVECTIVE FLUXES of free calcium, calcium-citrate complexes, and free citrate | Jconv__Cafree(c) = −C__Cafree__forconvection(c) * UFR(c)<br>Jconv__CaCi(c) = −C__CaCi__forconvection(c) * UFR(c)<br>Jconv__Cifree(c) = −C__Cifree__forconvection(c) * UFR(c) |
| TOTAL FLUXES | |
| Total calcium flux | Jdiff__CaT(c) = Jdiff__CaCi(c) + Jdiff__Cafree(c)<br>Jconv__CaT(c) = Jconv__Cafree(c) + Jconv__CaCi(c)<br>Jtotal__CaT(c) = Jdiff__CaT(c) + Jconv__CaT(c) |
| Total citrate flux | Jdiff__CiT(c) = Jdiff__CaCi(c) + Jdiff__Cifree(c)<br>Jconv__CiT(c) = Jconv__CaCi(c) + Jconv__Cifree(c)<br>Jtotal__CiT(c) = Jdiff__CiT(c) + Jconv__CiT(c) |
| Post-filter concentrations of total calcium and total citrate | Qpw__loc3(c) = Qpw__loc2(c) − UFR(c)<br>C__CaT__loc3(c) = ((C__CaT__loc2(c) * Qpw__loc2(c)) + Jtotal__CaT(c)) / (Qpw__loc3(c))<br>C__CiT__loc3(c) = ((C__CiT__loc2(c) * Qpw__loc2(c)) + Jtotal__CiT(c)) / (Qpw__loc3(c)) |
| Equilibrated post-filter concentrations of free calcium, free citrate, and calcium-citrate complexes | hc_factor(c) = Qpw__loc3(c) / Qpw__loc2(c)<br>C__bindingsites__loc3(c) = C__bindingsites__loc2(c) / hc_factor(c)<br><br>' Goal seek for post-filter ionized Ca (loc3)<br>rng__gs__iCa.Value = gs__iCa__default__loc3<br>rng__gs__C__CiT.Value = C__CiT__loc3(c)<br>rng__gs__C__bindingsites.Value = C__bindingsites__loc3(c)<br>rng__gs__C__CaT.Value = C__CaT__loc3(c)<br>rng__gs__cubic.GoalSeek Goal:=0, ChangingCell:=rng__gs__iCa<br>C__Cafree__loc3(c) = rng__gs__iCa.Value<br>C__CaCi__loc3(c) = ((C__Cafree__loc3(c) * C__CiT__loc3(c)) / (K__CaCi + C__Cafree__loc3(c)))<br>C__Cifree__loc3(c) = C__CiT__loc3(c) − C__CaCi__loc3(c) |
| Read current calcium infusion rate [l/min] | Rate__Ca__infusion(c) = Application.WorksheetFunction.VLookup(time(c), rng__Ca__infusion, 2, True) / (60000) |
| Blood and plasma water flow rates at loc4, and the plasma water to whole blood ratio at loc4 | Qpw__loc4(c) = Qpw__loc3(c) + Rate__Ca__infusion(c)<br>Qb__loc4(c) = Qb__loc1(c) + Rate__Ci__infusion(c) − UFR(c) + Rate__Ca__infusion(c)<br>R_pw_wb__loc4(c) = Qpw__loc4(c) / Qb__loc4(c) |
| Post-calcium-infusion concentrations of total calcium and total citrate | C__CaT__loc4(c) = (C__CaT__loc3(c) * Qpw__loc3(c) + C__Ca__infusion * Rate__Ca__infusion(c)) / Qpw__loc4(c)<br>C__CiT__loc4(c) = (C__CiT__loc3(c) * Qpw__loc3(c)) / Qpw__loc4(c) |
| Plasma flow rate at loc 4 | Qp__loc4(c) = Qp__loc1(c) + Rate__Ci__infusion(c) − UFR(c) + Rate__Ca__infusion(c) |
| Protein concentration at loc4 | C__prot__loc4(c) = C__prot__loc1(c) / (Qp__loc4(c) / Qp__loc1(c)) |
| Ratio of plasma to whole blood at loc4 | R_p_wb__loc4(c) = Qp__loc4(c) / Qb__loc4(c) |
| Hematocrit at location 4 | Hct__loc4(c) = (Qb__loc4(c) − Qp__loc4(c)) / Qb__loc4(c) |
| Theoretical whole blood concentrations of relevant solutes (used for access recirculation) | C__CaT__loc4__wb(c) = C__CaT__loc4(c) * R_pw_wb__loc4(c)<br>C__CiT__loc4__wb(c) = C__CiT__loc4(c) * R_pw_wb__loc4(c)<br>C__prot__loc4__wb(c) = C__prot__loc4(c) * R_p_wb__loc4(c) |
| Equilibrated post-calcium-infusion concentrations of free calcium, free citrate, and calcium-citrate complexes | hc_factor(c) = Qpw__loc4(c) / Qpw__loc3(c)<br>C__bindingsites__loc4(c) = C__bindingsites__loc3(c) / hc_factor(c)<br><br>rng__gs__iCa.Value = gs__iCa__default__loc4<br>rng__gs__C__CiT.Value = C__CiT__loc4(c) |

TABLE II-continued

Sample code (VBA) for Simulation Mode 1
Note: This excerpt is intended to illustrate one possible implementation of the key elements of the model (simulation mode 1). Certain steps (e.g., re-dimensioning arrays, setting certain variables prior to first use, procedure for routing to specified simulation mode, calculation of cumulative parameters such as mass balances, reporting simulation results, etc.) are omitted.
Simulation modes 2 and 3 are also omitted, as they are adaptations of the presented code, and their implementation will be straightforward to a reader skilled in the art.

| | |
|---|---|
| | rng__gs__C__bindingsites.Value = C__bindingsites__loc4(c) |
| | rng__gs__C__CaT.Value = C__CaT__loc4(c) |
| | rng__gs__cubic.GoalSeek Goal:=0, ChangingCell:=rng__gs__iCa |
| | C__Cafree__loc4(c) = rng__gs__iCa.Value |
| | C__CaCi__loc4(c) = ((C__Cafree__loc4(c) * C__CiT__loc4(c)) / (K__CaCi + C__Cafree__loc4(c))) |
| | C__Cifree__loc4(c) = C__CiT__loc4(c) − C__CaCi__loc4(c) |
| ECV at beginning of interval | ECV__beg(c) = ECV__end(c − 1) |
| Amounts of citrate and calcium in ECV at beginning of interval | N__CiT__ECV__beg(c) = C__CiT__sys__beg(c) * ECV__beg(c) <br> N__CaT__ECV__beg(c) = C__CaT__sys__beg(c) * ECV__beg(c) |
| Amounts of citrate and calcium infused during interval | N__CiT__infused__interval(c) = Rate__Ci__infusion(c) * C__Ci__infusion * interval <br> N__CaT__infused__interval(c) = Rate__Ca__infusion(c) * C__Ca__infusion * interval |
| Net systemic changes in total citrate and total calcium during interval | dN__CiT__systemic__interval(c) = (Jtotal__CiT(c) * interval) + N__CiT__infused__interval(c) <br> dN__CaT__systemic__interval(c) = (Jtotal__CaT(c) * interval) + N__CaT__infused__interval(c) |
| Amount of citrate in ECV at end of interval, not considering citrate generation or metabolism | N__CiT__ECV__end__noMETnoG(c) = N__CiT__ECV__beg(c) + dN__CiT__systemic__interval(c) |
| Amount of total calcium in ECV at end of interval, not considering buffering. Note that this is the unbuffered amount for this particular interval, but it is the buffered amount that is carried forward to the beginning of the next interval, which will be different if KMP is not equal to 0. | N__CaT__ECV__end__prebuffering(c) = N__CaT__ECV__beg(c) + dN__CaT__systemic__interval(c) |
| | UF__interval(c) = UFR(c) * interval <br> Vol__Ci__infusion__interval(c) = Rate__Ci__infusion(c) * interval <br> Vol__Ca__infusion__interval(c) = Rate__Ca__infusion(c) * interval |
| ECV at end of interval | ECV__end(c) = ECV__beg(c) − UF__interval(c) + Vol__Ci__infusion__interval(c) + Vol__Ca__infusion__interval(c) |
| Citrate generation during interval | G__Ci__interval(c) = ((Rate__G__Ci * interval) / (24 * 60)) / (192.12352) |
| Amount of citrate in ECV at end of interval, considering citrate generation but not metabolism | N__CiT__ECV__end__noMET(c) = N__CiT__ECV__end__noMETnoG(c) + G__Ci__interval(c) |
| Citrate concentration in ECV at end of interval, considering citrate generation but not metabolism | C__CiT__ECV__end__noMET(c) = N__CiT__ECV__end__noMET(c) / ECV__end(c) <br> average__C__CiT__sys__interval(c) = WorksheetFunction.Average(C__CiT__ECV__end__noMET(c), C__CiT__sys__beg(c)) |
| Amount of citrate metabolized during interval | N__Ci__metabolized__interval(c) = N__CiT__ECV__end__noMET(c) − (average__C__CiT__sys__interval(c) * Exp(−k__Ci * interval) * WorksheetFunction.Average(ECV__end(c), ECV__beg(c))) |
| Amount of citrate in ECV at end of interval, considering generation and metabolism | N__CiT__ECV__end(c) = N__CiT__ECV__end__noMET(c) − N__Ci__metabolized__interval(c) |
| Total systemic citrate conc. at end of interval | C__CiT__sys__end(c) = N__CiT__ECV__end(c) / ECV__end(c) |
| Mobilization/sequestration of calcium during interval | MCa(c) = −((Jdiff__CaT(c) * interval) + N__CaT__infused__interval(c)) * KMP |
| Total systemic calcium concentration at end of interval | C__CaT__sys__end(c) = (N__CaT__ECV__end__prebuffering(c) + MCa(c)) / ECV__end(c) |
| ECV contraction factor | ECV__contractionfactor__interval(c) = ECV__beg(c) / ECV__end(c) |
| Goal seek for systemic ionized Ca at beginning of interval | rng__gs__iCa.Value = gs__iCa__default__sys <br> rng__gs__C__CiT.Value = C__CiT__sys__beg(c) <br> rng__gs__C__bindingsites.Value = C__bindingsites__sys__beg(c) <br> rng__gs__C__CaT.Value = C__CaT__sys__beg(c) <br> rng__gs__cubic.GoalSeek Goal:=0, ChangingCell:=rng__gs__iCa <br> C__Cafree__sys__beg(c) = rng__gs__iCa.Value |

TABLE II-continued

Sample code (VBA) for Simulation Mode 1
Note: This excerpt is intended to illustrate one possible implementation of the key elements of the model (simulation mode 1). Certain steps (e.g., re-dimensioning arrays, setting certain variables prior to first use, procedure for routing to specified simulation mode, calculation of cumulative parameters such as mass balances, reporting simulation results, etc.) are omitted.
Simulation modes 2 and 3 are also omitted, as they are adaptations of the presented code, and their implementation will be straightforward to a reader skilled in the art.

| | |
|---|---|
| +1 in order to fill all the parameters for the end-of-HD time point that would not otherwise get calculated in the post-HD iterations (such as pre-/post-filter values). Then, the counter is decreased by one and and the program flow routed to the post-HD iterations. Since these parameters from the additional iteration will not be overwritten, they can be used for plotting/reporting. | Loop Until c = req_iterations − req_iterations_post + 1<br>  c = c − 1 ' See note in the line above<br><br>GoTo post_HD_iterations |
| POSTDIALYTIC ITERATIONS (COMMON TO ALL SIMULATIONS) | post_HD_iterations: |
| Set interval length | interval = interval_post<br>c = c + 1<br>time(c) = time(c − 1) + interval_intra<br>GoTo loop_post_HD<br>Do<br>  c = c + 1<br>  time(c) = time(c − 1) + interval<br>loop_post_HD: |
| Total systemic calcium and citrate concentrations at beginning of interval | C_CaT_sys_beg(c) = C_CaT_sys_end(c − 1)<br>C_CiT_sys_beg(c) = C_CiT_sys_end(c − 1) |
| Systemic concentration of total protein | C_prot_sys_beg(c) = C_prot_sys_beg(c − 1) *<br>  ECV_contractionfactor_interval(c − 1) |
| Systemic concentration of binding sites at beginning of interval | C_bindingsites_sys_beg(c) = (12 * C_prot_sys_beg(c) / 69000) * 1000 |
| Systemic hematocrit at beginning of interval | Hct_sys(c) = Hct_sys(c − 1) / (Hct_sys(c − 1) + ((1 − Hct_sys(c − 1)) /<br>  ECV_contractionfactor_interval(c − 1))) |
| ECV at beginning of interval | ECV_beg(c) = ECV_end(c − 1) |
| Amounts of citrate and calcium in ECV at beginning of interval | N_CiT_ECV_beg(c) = C_CiT_sys_beg(c) * ECV_beg(c)<br>N_CaT_ECV_beg(c) = C_CaT_sys_beg(c) * ECV_beg(c) |
| Amounts of citrate in ECV at end of interval, not considering citrate generation or metabolism | N_CiT_ECV_end_noMETnoG(c) = N_CiT_ECV_beg(c) |
| Amount of total calcium in ECV at end of interval, not considering buffering. Note that this is the unbuffered amount for this particular interval, but it is the buffered amount that is carried forward to the beginning of the next interval, which will be different if KMP is not equal to 0. | N_CaT_ECV_end_prebuffering(c) = N_CaT_ECV_beg(c) +<br>  dN_CaT_systemic_interval(c) |
| ECV at end of interval | ECV_end(c) = ECV_beg(c) |
| Citrate generation during interval | G_Ci_interval(c) = ((Rate_G_Ci * interval) / (24 * 60)) / (192.12352) |
| Amount of citrate in ECV at end of interval, considering citrate generation but not metabolism | N_CiT_ECV_end_noMET(c) = N_CiT_ECV_end_noMETnoG(c) +<br>  G_Ci_interval(c) |
| Citrate concentration in ECV at end of interval, considering citrate generation but not metabolism | C_CiT_ECV_end_noMET(c) = N_CiT_ECV_end_noMET(c) / ECV_end(c)<br>average_C_CiT_sys_interval(c) =<br>  WorksheetFunction.Average(C_CiT_ECV_end_noMET(c),<br>  C_CiT_sys_beg(c)) |
| Amount of citrate metabolized during interval | N_Ci_metabolized_interval(c) = N_CiT_ECV_end_noMET(c) −<br>  (average_C_CiT_sys_interval(c) * Exp(−k_Ci * interval) *<br>  WorksheetFunction.Average(ECV_end(c), ECV_beg(c))) |

TABLE II-continued

Sample code (VBA) for Simulation Mode 1
Note: This excerpt is intended to illustrate one possible implementation of the key elements of the model (simulation mode 1). Certain steps (e.g., re-dimensioning arrays, setting certain variables prior to first use, procedure for routing to specified simulation mode, calculation of cumulative parameters such as mass balances, reporting simulation results, etc.) are omitted.
Simulation modes 2 and 3 are also omitted, as they are adaptations of the presented code, and their implementation will be straightforward to a reader skilled in the art.

| | |
|---|---|
| Amount of citrate in ECV at end of interval, considering generation and metabolism | N_CiT_ECV_end(c) = N_CiT_ECV_end_noMET(c) − N_Ci_metabolized_interval(c) |
| Total systemic citrate conc. at end of interval | C_CiT_sys_end(c) = N_CiT_ECV_end(c) / ECV_end(c) |
| Mobilization/sequestration of calcium during interval | MCa(c) = −((Jdiff_CaT(c) * interval) + N_CaT_infused_interval(c)) * KMP |
| Total systemic calcium concentration at end of interval | C_CaT_sys_end(c) = (N_CaT_ECV_end_prebuffering(c) + MCa(c)) / ECV_end(c) |
| ECV contraction factor | ECV_contractionfactor_interval(c) = ECV_beg(c) / ECV_end(c) |
| Goal seek for systemic ionized Ca at beginning of interval | rng_gs_iCa.Value = gs_iCa_default_sys<br>rng_gs_C_CiT.Value = C_CiT_sys_beg(c)<br>rng_gs_C_bindingsites.Value = C_bindingsites_sys_beg(c)<br>rng_gs_C_CaT.Value = C_CaT_sys_beg(c)<br>rng_gs_cubic.GoalSeek Goal:=0, ChangingCell:=rng_gs_iCa<br>C_Cafree_sys_beg(c) = rng_gs_iCa.Value<br>Loop Until c = req_iterations |

The relevant teachings of all patents, patent applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of performing regional citrate anticoagulant dialysis of a patient's blood comprising:
   a) flowing blood from and back to the patient through an extracorporeal dialysis circuit including a dialyzer having semi-permeable dialysis membranes and a dialysate chamber surrounding the membranes;
   b) flowing a dialysate containing calcium and citrate through the dialysate chamber of the dialyzer, the amount of calcium contained in the dialysate sufficient to eliminate the need for calcium to be added to the patient's blood downstream of the dialyzer;
   c) predicting a systemic ionized calcium concentration in the blood of the patient to assess safety of the systemic ionized calcium concentration for the patient using a mathematical model including
      i) employing citrate generation and metabolism to determine resulting citrate and calcium equilibria,
      ii) determining citrate and calcium concentration changes caused by recirculation,
      iii) determining a required pre-dialyzer citrate concentration and resulting citrate and calcium concentrations,
      iv) determining a dialysate composition,
      v) determining diffusive and convective dialyzer fluxes,
      vi) determining post-dialyzer citrate and calcium concentrations; and
   d) introducing citrate into the patient's blood upstream of the dialyzer in a sufficient amount to reduce clotting of the patient's blood in the extracorporeal dialysis circuit, whereby the patient's blood is dialyzed.

2. The method of claim 1, wherein the citrate comprises sodium citrate.

3. The method of claim 1, wherein the citrate comprises sodium isocitrate.

4. The method of claim 1, wherein the step of introducing the citrate includes time periods when the amount of citrate is modulated downwardly, alternating with time periods when the amount of citrate is modulated upwardly.

5. The method of claim 1, wherein the step of introducing the citrate is computer controlled, including using a processor to computationally determine one or more amounts of citrate during dialysis treatment of a patient, the processor coupled between the patient and the dialyzer.

6. The method of claim 4, further including the step of flushing the dialysis membranes during the time periods when the amount is modulated downwardly.

7. The method of claim 6, wherein the dialysis membranes are flushed with a liquid selected from the group consisting of bicarbonate containing dialysate, lactate containing dialysate, acetate containing dialysate, calcium containing dialysate, calcium and citrate anticoagulant containing dialysate, dextrose solutions, and saline.

8. The method of claim 1, wherein the step of introducing the citrate is followed by introducing heparin into the extracorporeal dialysis circuit.

9. The method of claim 1, further including using the mathematical model to yield a preliminary predicted post-dialysis systemic ionized calcium concentration.

10. The method of claim 9, further including statistically correcting the preliminary predicted post-dialysis concentration of systemic ionized calcium in the patient's blood to provide a final predicted post-dialysis systemic ionized calcium concentration.

11. The method of claim 10, wherein statistically correcting the preliminary predicted post-dialysis concentration of systemic ionized calcium in the patient's blood includes:
   1) classifying the patient's parathyroid hormone (PTH) level into at least two categories of PTH levels based on PTH concentration; and
   2) estimating a difference between the preliminary predicted post-dialysis concentration and the actual post-dialysis concentration of systemic ionized calcium in the patient's blood based on the category of the PTH level of the patient, dialysis treatment time, and the preliminary predicted post-dialysis concentration of systemic ionized calcium, thereby obtaining a correction to the preliminary predicted post-dialysis concentration of systemic ionized calcium in the patient's blood.

12. The method of claim 11, wherein the difference between the preliminary predicted and actual concentration of post-dialysis systemic ionized calcium in the patient's blood is determined by employing a multivariate linear regression model including the category of the PTH level of the patient, dialysis treatment time, and the preliminary predicted post-dialysis concentration of systemic ionized calcium in the patient's blood as predictors.

13. The method of claim 11, wherein the at least two categories of PTH levels are tertiles.

14. The method of claim 10, wherein statistically correcting the preliminary predicted post-dialysis concentration of systemic ionized calcium in the patient's blood includes:
  1) classifying the patient's alkaline phosphatase (AP) level into at least two categories of AP levels based on AP concentration; and
  2) estimating a difference between the preliminary predicted post-dialysis concentration and the actual post-dialysis concentration of systemic ionized calcium in the patient's blood based on the category of the AP level of the patient, dialysis treatment time, and the preliminary predicted post-dialysis concentration of systemic ionized calcium, thereby obtaining a correction to the preliminary predicted post-dialysis concentration of systemic ionized calcium in the patient's blood.

15. The method of claim 14, wherein determining the difference between the preliminary predicted post-dialysis concentration and actual post-dialysis concentration of systemic ionized calcium in the patient's blood includes employing a multivariate linear regression model including the category of the AP level of the patient, dialysis treatment time, and the preliminary predicted post-dialysis concentration of systemic ionized calcium in the patient's blood as predictors.

16. The method of claim 14, wherein the at least two categories of AP levels are tertiles.

17. The method of claim 10, wherein statistically correcting the preliminary predicted concentration of systemic ionized calcium in the patient's blood is performed for any time point during dialysis and includes:
  1) classifying the patient's parathyroid hormone (PTH) level into at least two categories of PTH levels based on PTH concentration; and
  2) estimating a difference between the preliminary predicted concentration and the actual concentration of systemic ionized calcium in the patient's blood for any time point during the dialysis treatment, thereby obtaining a correction to the preliminary predicted concentration of systemic ionized calcium in the patient's blood.

18. The method of claim 17, wherein the difference between the preliminary predicted and the actual concentration of systemic ionized calcium in the patient's blood is determined by estimating a slope of the relationship between a prediction error, obtained from the preliminary predicted systemic ionized calcium concentration minus the actual measured systemic ionized calcium concentration, and the elapsed time of dialysis, and multiplying the slope by the elapsed time of dialysis for the time point of interest.

19. The method of claim 18, wherein the prediction error slope is estimated by employing a multivariate linear regression model including the category of PTH level of the patient and the preliminary predicted post-dialysis concentration of systemic ionized calcium in the patient's blood as predictors.

20. The method of claim 17, wherein the at least two categories of PTH levels are tertiles.

21. The method of claim 10, wherein statistically correcting the preliminary predicted concentration of systemic ionized calcium in the patient's blood is performed for any time point during dialysis and includes:
  1) classifying the patient's alkaline phosphatase (AP) level into at least two categories of AP levels based on AP concentration; and
  2) estimating a difference between the preliminary predicted post-dialysis concentration and the actual concentration of systemic ionized calcium in the patient's blood for any time point during dialysis, thereby obtaining a correction to the preliminary predicted post-dialysis concentration of systemic ionized calcium in the patient's blood.

22. The method of claim 21, wherein the difference between the preliminary predicted and the actual concentration of systemic ionized calcium in the patient's blood is determined by estimating a slope of the relationship between a prediction error, obtained from the preliminary predicted systemic ionized calcium concentration minus the actual measured systemic ionized calcium concentration, and the elapsed time of dialysis, and multiplying the slope by the elapsed time of dialysis for the time point of interest.

23. The method of claim 22, wherein the prediction error slope is estimated by employing a multivariate linear regression model including the category of AP level of the patient and the preliminary predicted post-dialysis concentration of systemic ionized calcium in the patient's blood as predictors.

24. The method of claim 21, wherein the at least two categories of AP levels are tertiles.

* * * * *